United States Patent
Noshi et al.

(10) Patent No.: US 7,885,374 B2
(45) Date of Patent: Feb. 8, 2011

(54) X-RAY CT APPARATUS, A METHOD FOR CHANGING THE HELICAL PITCH, AN IMAGE RECONSTRUCTION PROCESSING APPARATUS, AN IMAGE RECONSTRUCTION PROCESSING METHOD, AND AN IMAGE RECONSTRUCTION PROCESSING PROGRAM

(75) Inventors: Yasuhiro Noshi, Nasushiobara (JP); Tatsuo Maeda, Otawara (JP); Miwa Okumura, Utsunomiya (JP); Shinsuke Tsukagoshi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 511 days.

(21) Appl. No.: 11/685,985

(22) Filed: Mar. 14, 2007

(65) Prior Publication Data

US 2007/0217567 A1     Sep. 20, 2007

(30) Foreign Application Priority Data

Mar. 15, 2006  (JP) .............................. 2006-071057

(51) Int. Cl.
*A61B 6/03* (2006.01)
(52) U.S. Cl. .................. 378/8; 378/4; 378/15
(58) Field of Classification Search ............ 378/4, 378/8, 15; 600/431
See application file for complete search history.

(56) References Cited

U.S. PATENT DOCUMENTS

| | | | | |
|---|---|---|---|---|
| 5,390,112 A * | 2/1995 | Tam | ............................ | 378/17 |
| 6,256,366 B1 * | 7/2001 | Lai | ............................... | 378/4 |
| 6,353,653 B1 * | 3/2002 | Edic | .............................. | 378/8 |
| 6,421,411 B1 | 7/2002 | Hsieh | | |
| 6,721,386 B2 * | 4/2004 | Bulkes et al. | ................... | 378/8 |
| 2003/0163039 A1 * | 8/2003 | Pan et al. | ..................... | 600/425 |

(Continued)

FOREIGN PATENT DOCUMENTS

EP     1 712 181 A2    10/2006

(Continued)

OTHER PUBLICATIONS

Hsieh, Computed Tomography: Principles, Designs, Artifacts and Recent Advances, 2003, SPIE Press, ISBN 0-8194-4425-1, pp. 288-292.*

(Continued)

*Primary Examiner*—Edward J Glick
*Assistant Examiner*—John M Corbett
(74) *Attorney, Agent, or Firm*—Oblon, Spivak, McClelland, Maier & Neustadt, L.L.P.

(57) ABSTRACT

An X-ray computed tomography (CT) apparatus having an X-ray tube emitting an X-ray, a detector detecting X-rays transmitted through a subject to be examined, and a bed on which said subject to be examined is placed, said X-ray CT apparatus reconstructing the image of the subject to be examined from a transmission data obtained by emitting X-rays to the subject to be examined. The X-ray computed tomography (CT) apparatus further having an input part, a scan controlling part, a detecting part, a memory part, a segmentation part, a biological-signal synchronization reconstructing part, a biological-signal asynchronization reconstructing part, and a combining part.

17 Claims, 20 Drawing Sheets

U.S. PATENT DOCUMENTS

| | | | |
|---|---|---|---|
| 2005/0074091 A1 | 4/2005 | Tsujii | |
| 2005/0089133 A1 | 4/2005 | Tsuyuki | |
| 2005/0158740 A1* | 7/2005 | Shemesh et al. | 435/6 |
| 2005/0175140 A1* | 8/2005 | Tsujii | 378/4 |
| 2006/0034419 A1* | 2/2006 | Nishide et al. | 378/15 |
| 2006/0262896 A1 | 11/2006 | Nishide et al. | |
| 2007/0092057 A1* | 4/2007 | Bruder et al. | 378/15 |

FOREIGN PATENT DOCUMENTS

| | | |
|---|---|---|
| JP | 2003-275200 | 9/2003 |
| JP | 2004208715 A * | 7/2004 |
| JP | 2005-66042 | 3/2005 |
| WO | WO 2004100791 A1 * | 11/2004 |

OTHER PUBLICATIONS

PTO 09-8184, Oct. 2009, English translation for JP 2004208715 A.*

* cited by examiner

FIG. 17A
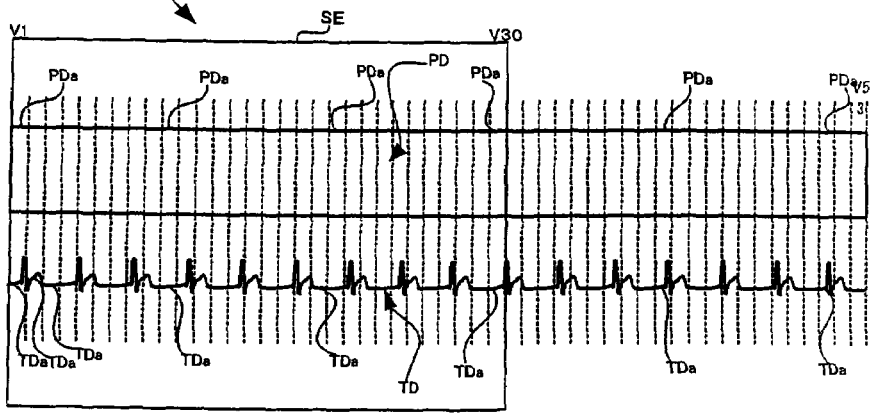
FIG. 17B
FIG. 17C
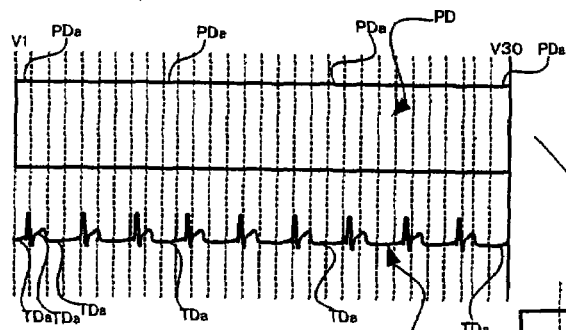
FIG. 17D
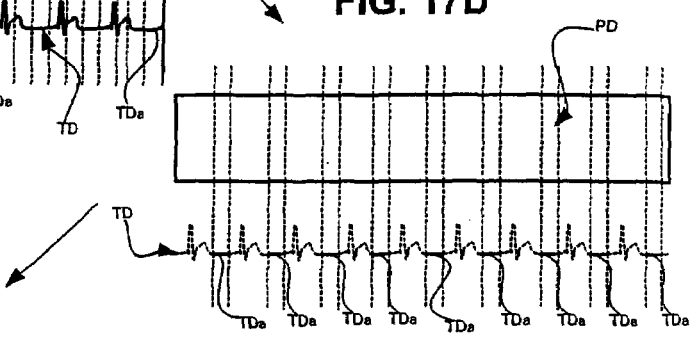
FIG. 17E
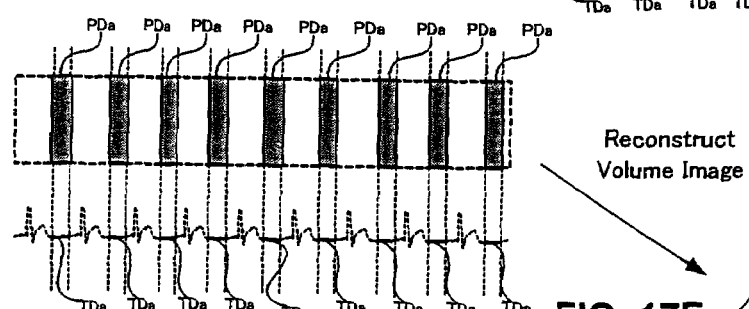
Reconstruct Volume Image
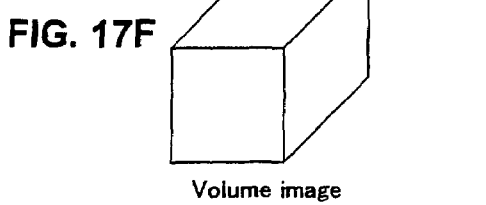
FIG. 17F
Volume image

FIG. 18A
Biological signal asynchronization reconstruction area V1~V30
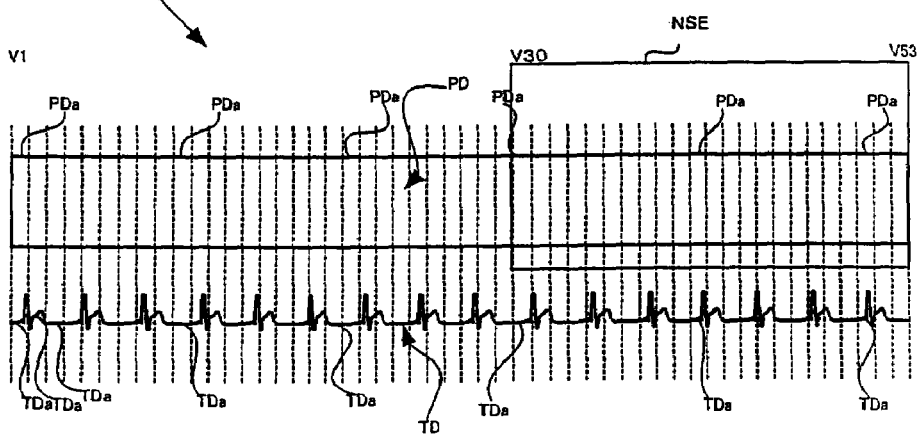
FIG. 18B
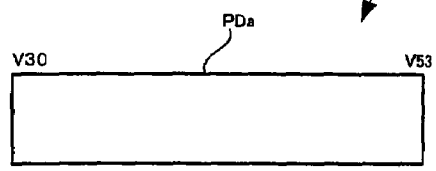
FIG. 18C
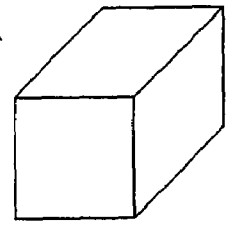
FIG. 18D

X-RAY CT APPARATUS, A METHOD FOR CHANGING THE HELICAL PITCH, AN IMAGE RECONSTRUCTION PROCESSING APPARATUS, AN IMAGE RECONSTRUCTION PROCESSING METHOD, AND AN IMAGE RECONSTRUCTION PROCESSING PROGRAM

BACKGROUND OF THE INVENTION

1. Field of the Invention

The present invention relates to a technology for emitting an X-ray while changing the helical pitch so as to obtain transmission data for a subject to be examined, reconstructing an image of the subject to be examined from the obtained transmission data.

2. Description of the Related Art

The X-ray CT apparatus emits X-rays, detects X-rays transmitted through the subject to be examined, and reconstructs the image of the inside of the subject to be examined from projection data indicating the intensity of detected X-rays. It plays an important role in medical practices such as diagnosing diseases, treatment, planning surgery, and so forth. This X-ray CT apparatus has a variety of imaging methods, depending on the type of diagnostic imaging, including the method of administering a contract agent to the subject to be examined and then obtaining the image and the method of reconstructing the image in synchronization with the biological signal, for example. In any case, it is essential to obtain an image that is accurate enough for diagnostic imaging and to reconstruct the same.

In a method of administering a contract agent to the subject to be examined before obtaining the image, a pre-scan is performed, and then a scan is initiated after detecting that the contract agent has flowed into the area of which the image is to be reconstructed by this pre-scan. For contract-agent imaging of X-ray CT apparatus, it is essential to perform a scan while the contract agent administered to the subject to be examined has flowed into the reconstruction area of the image. Therefore, a pre-scan is repeated before the scan. This pre-scan scans part of the reconstruction area of an image with a lower radiation dose than the actual scan and determines concentration of contract agent flowing into the reconstruction area of an image depending upon the CT value of the obtained image. Once concentration of the contract agent reaches a certain point, the scan is initiated. The method of automatically determining the concentration of the contract agent by way of a predetermined threshold value and then automatically initiating the scan is referred to a "real prep-scan" (e.g., cf. Japanese Patent laid-open No. 2003-245275).

This real-prep scanning by a conventional X-ray CT apparatus is shown in FIG. 1. As shown in FIG. 1, first, an X-ray tube is positioned for a pre-scan at a point within the reconstruction area of the image, and then X-rays is emitted at the pre-scan position $Z_0$ to obtain a pre-scan image. This pre-scan image is a tomographic image. Once the pre-scan image is obtained, the CT value of this image is calculated, and if it is at the threshold value or greater, the scan can be initiated.

For the scan, first, the bed is moved so that X-ray tube is positioned outside the reconstruction area of the image, and then a margin is set outside the starting edge of the reconstruction area of the image. After the margin is set, the scan is initiated from this margin area toward the ending edge of the reconstruction area of the image by the helical scan. The reason to set the margin is that X-rays for the number of views (BPview) required for reconstruction of the image is also emitted at the starting edge position of the image reconstruction by a helical scan. This is because, when the scan is initiated from the pre-scan position $Z_0$ directly to the ending edge of the reconstruction area of the image, it is sometimes impossible to ensure the emission of X-rays for BPview at the starting edge position of the image reconstruction, which is often outside the pre-scan position $Z_0$.

For the real prep-scan, it is essential to scan at the time when the contract agent administered to the subject to be examined is flowing into the reconstruction area of the image. Therefore, it is important to perform the scan immediately after the pre-scan detects that the contract agent has flowed into the area. This is because, if the contract agent flows out of the reconstruction area of the image or is lost and the necessary concentration of the contract agent thus cannot be obtained, an image with superior quality cannot be reconstructed. However, as mentioned above, for a conventional real prep-scan, when the pre-scan detects the flow of the contract agent, X-ray tube must be placed outside the reconstruction area of the image, the margin must be formed, and the scan must then be initiated from this margin. In short, the initiation of the scan for the reconstruction area of the image must be suspended from the time of detection of flowing of the contract agent due to this margin setting and the scan of the margin. Accordingly, with a conventional real prep-scan, an image with sufficient accuracy is not necessarily reconstructed. Furthermore, X-rays is emitted at the area that corresponds to the margin as well, so the subject to be examined will be affected by exposure even when he is outside the reconstruction area of the image, which is also not desirable for the subject to be examined.

Moreover, diagnostic imaging includes an approach to diagnose only the region of interest and an approach to diagnose a larger area e.g. searching the affected area from the entire body. For such an approach to diagnose the larger area, the reconstruction area of the image may include an area involving physical movement such as from the heart, lungs, and so forth, and an area without such physical movement. The physical movement corresponds to the movement of activities of the body system. Between the area involving physical movement and areas without physical movement, the method of obtaining data required to reconstruct the image for that area is different.

For areas involving physical movement of the heart, lungs, and so forth, a biological signal synchronization reconstruction method that is characteristic of the method of obtaining data required for reconstruction is used (e.g., cf. Japanese Patent laid-open No. 2005-66042).

According to the biological signal synchronization reconstruction method, biological signal data showing changes in the physical movement is obtained in synchronization with the imaging of a subject to be examined, and then, partial data obtained while obtaining the biological signal data showing movement of a particular phase is extracted from projection data and gathered, and then the gathered data is used to reconstruct the image. The helical pitch is limited to the pitch that passes the area involving an area of physical movement when multiple cycles of a changing biological signal are repeated, in order to gather multiple sets of data showing the physical movement of the particular phase.

Accordingly, to image an area that includes an area involving movement and an area without movement, it has been necessary to perform a separate scan by segmenting the reconstruction area of the image into an area involving movement and an area without movement, because methods of obtaining projection data required for reconstructing the image are different.

FIG. 2 is a view showing a method of imaging a conventional area including an area involving physical movement and an area without physical movement. The reconstruction area SE, which involves physical movement and is reconstructed in synchronization with the biological signal, is included in the entire reconstruction area of the image and is situated between reconstruction areas NSE that do not involve physical movement and are reconstructed in asynchronization with the biological signal. In this case, the first scan images one of the reconstruction areas NSE that is reconstructed in asynchronization with the biological signal. Second, it images the reconstruction area SE that is reconstructed in synchronization with the biological signal by a second scan. Furthermore, it images another reconstruction area NSE that is reconstructed in asynchronization with the biological signal by a third scan.

Then, it reconstructs the projection data obtained by the first and third scans in asynchronization with physical movement into the volume image, and also reconstructs the projection data obtained by the second scan into the volume image by the biological signal synchronization reconstruction method.

In addition, there is sometimes a demand to display an image of areas that are obtained as a whole so as to observe the inside of the subject to be examined body overall. This is, for example, the case when contract agent is administered to the subject to be examined in order to observe the overall blood circulation.

However, when there is both a reconstruction area SE that involves physical movement and a reconstruction area NSE without physical movement in the area to be imaged, in order to image these areas separately, there is a time lag between the image of the reconstruction area SE involving physical movement and the image of the reconstruction area NSE without physical movement. As a result, the concentration of the contract agent appears uneven, depending on the area being observed. This makes it difficult to totally diagnose from the imaged areas, even if such areas are displayed as a whole. Furthermore, separate imaging of these areas means that the subject to be examined must be exposed to risk from radiation multiple times, which is not desirable. On the other hand, if the reconstruction area SE involving physical movement and the reconstruction area NSE without physical movement are imaged in a single simultaneous scan, and the resultant projection data is then not reconstructed by way of a biological signal synchronization reconstruction method, this leads to inaccurate data results around the area involving physical movement, thereby significantly decreasing the quality of the image.

SUMMARY OF THE INVENTION

The present invention relates to technology that forms an image of the inside of a subject to be examined from transmission data of the subject to be examined obtained by emitting X-rays, and is intended to provide technology that enables reconstruction of an image with superior quality that is effective in the application of diagnosis and also reduces the risk of the subject to be examined being exposed to excessive amounts of radiation.

In a first embodiment of the present invention, a pre-scan reconstructs a pre-scan image of the subject to be examined from transmission data based on X-rays detected by the detector. Based on changes in the CT value of the reconstructed pre-scan image, it is determined whether to initiate the scan. Based on this determination result, the scan is performed by directly changing the helical pitch from the stopped position of the bed for the pre-scan to the position toward the ending edge of the reconstruction area of the image, and then the scan image of the subject to be examined is reconstructed from the transmission data based on X-rays detected by the detector via the scan. The scan is initiated at the first helical pitch that enables the emission of X-rays for a predetermined number of views to the starting edge of the reconstruction area of the image, and after emitting X-rays for the predetermined number of views, the pitch is switched to a predetermined second helical pitch for continuation of the scan.

According to the first embodiment of the present invention, the margin is not needed to be set outside the reconstruction area of the image to obtain the image of the starting edge position, so unnecessary risk from radiation is thereby prevented. Furthermore, because the margin is set outside the bed, it is not needed to be moved backward once to form the margin outside the reconstruction area of the image, thus allowing initiation of the scan immediately after the pre-scan. Therefore, after detecting flowing of the contract agent, the scan can be initiated quickly, and an image with high accuracy can be reconstructed as a result of the contract effect from the contract agent.

It is noted that a predetermined number of views may be the number of views necessary to reconstruct an image at the starting edge of the reconstruction area of the image. Alternatively, it may be the number of views that is insufficient for construction of the image at the starting edge of the reconstruction area of the image if initiating the scan at the second helical pitch, and the first helical pitch may be the maximum pitch at which X-rays for the number of insufficient views can be emitted. On the other hand, it may be the number of views that is insufficient for construction of the image at the starting edge of the reconstruction area of the image if initiating the scan at the second helical pitch, and the value of the first helical pitch may be 0.

Furthermore, in advance, the first helical pitch at which X-rays for the predetermined number of views to the starting edge of the reconstruction area of the image can be emitted may be calculated. Moreover, for reconstructing the image via a scan, the image for the zone where the helical pitch is being changed may also be reconstructed.

The second embodiment of the present invention, first stores transmission data of the subject to be examined obtained by a continuous single helical scan and the biological signal data of the subject to be examined obtained during said helical scan in a correlated way. Then, the transmission data is segmented into a first transmission data that corresponds to the area to be reconstructed in synchronization with said biological signal and the second transmission data that corresponds to the area to be reconstructed in asynchronization with said biological signal. Next, based on said biological signal data and said first transmission data, while overlapping in the vicinity of the two boundaries, the image of the subject to be examined is reconstructed, in asynchronization with said biological signal data, and then the image of the subject to be examined is reconstructed from said second transmission data. Afterward, a combined image is formed in which the image reconstructed in synchronization with the biological signal and the image reconstructed in asynchronization with the biological signal are combined with weighting addition at the partly overlapped area.

According to the second embodiment of the present invention, when the scan is performed simultaneously for both the area involving physical movement and the area not involving physical movement, no time lag will be incurred over these areas, and the entire image can also be reconstructed without leading to inaccurate data around the area involving physical movement. Additionally, an image with superior quality can be obtained, without performing multiple scans, which also reduces the risk of effects from unnecessary radiation.

BRIEF DESCRIPTION OF THE DRAWINGS

FIG. 17 shows pattern diagrams of the biological signal synchronization reconstruction method.

FIG. 18 shows pattern diagrams of reconstruction in asynchronization with the biological signal.

DETAILED DESCRIPTION OF THE EMBODIMENT

Hereinafter, with reference to the drawings, the preferred embodiments of the technology for obtaining transmission data according to the present invention and technology for the process of image reconstruction are explained in detail below.

Embodiment for Obtaining Projection Data 1

Figure 1:
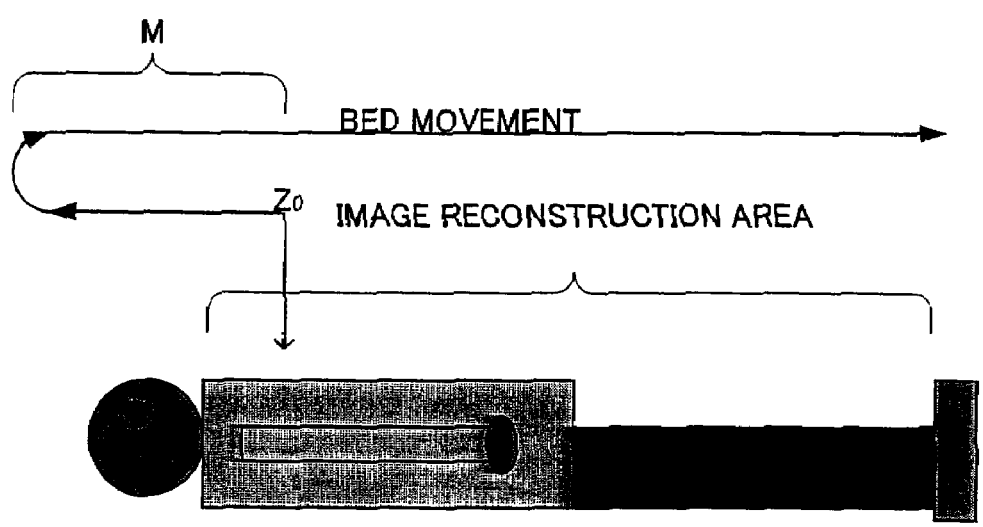
FIG. 1 shows a real preparatory scan by a conventional X-ray CT apparatus.
Figure 2:
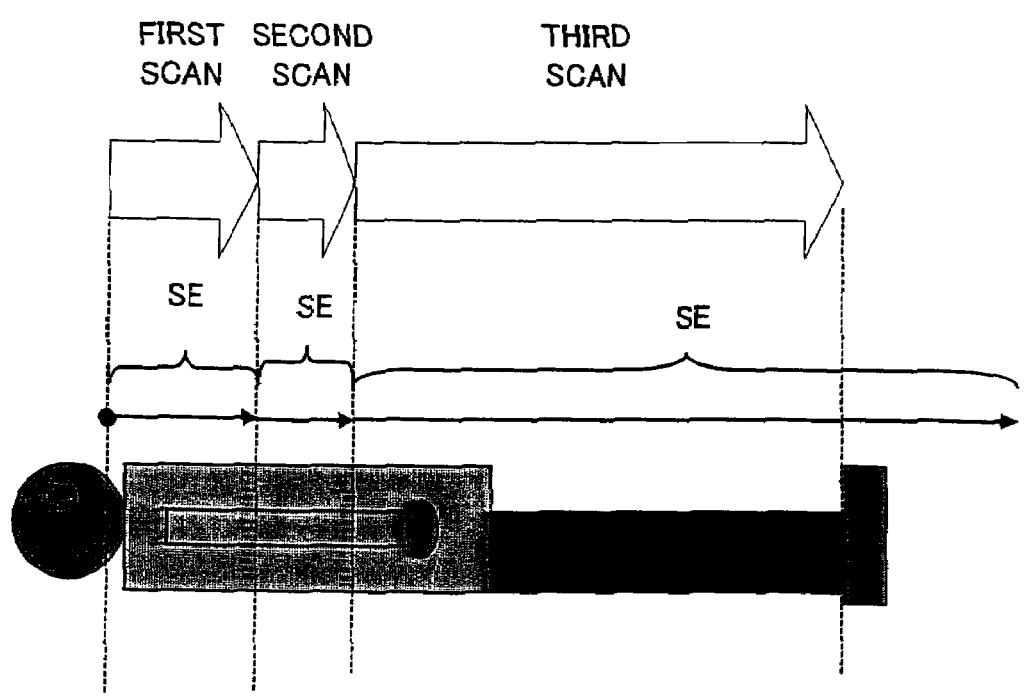
FIG. 2 shows technology for imaging the conventional area including an area with physical movement and an area without physical movement.
Figure 3:
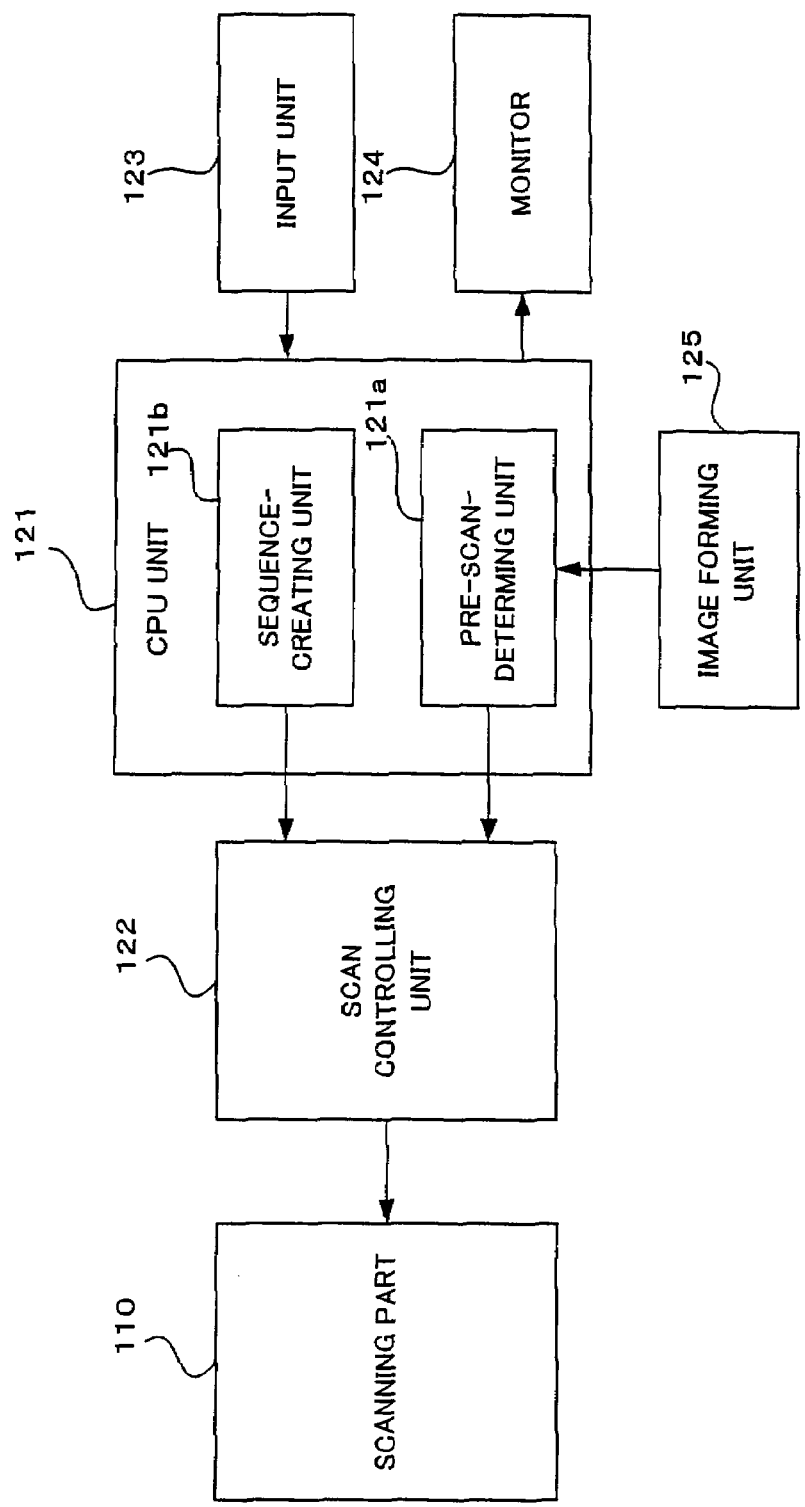
FIG. 3 shows the structure that controls the variable helical scan by X-ray CT apparatus according to the present embodiment.

FIG. 3 shows the structure for controlling the variable helical scan by a X-ray CT apparatus according to the present embodiment. The X-ray CT apparatus includes a scanning part 110, a CPU unit 121, and a scan-controlling unit 122. An input unit 123, a monitor 124, and an image forming unit 125 are connected to the CPU unit 121 to enable data input/output. Furthermore, the CPU unit 121 includes a pre-scan-determining unit 121a and a sequence-creating unit 121b.

This X-ray CT apparatus obtains, via a real prep-scan, an image of the reconstruction area of the image. First, it performs a pre-scan and then detects flowing of the contract agent to the reconstruction area of the image. The reconstruction area of the image is the area for which an image of the subject to be examined is to be reconstructed. During the pre-scan, in order to detect that the contract agent has reached the reconstruction area of the image, so part of the reconstruction area of the image is scanned with low-dose radiation. The CT value of the pre-scan image obtained with the low-dose radiation is monitored, and when the CT value reaches the predetermined threshold value, a scan of the reconstruction area of the image is initiated. The image in which the contract agent is used will have a higher CT value, so if the CT value exceeds the threshold value, it can be detected that the contract agent has reached the reconstruction area of the image. The scan is performed by emitting X-rays via a variable helical scan to obtain a scan image of the reconstruction area of the image.

When the pre-scan detects the flow of the contract agent, the X-ray CT apparatus begins to image the reconstruction area of the image via a variable helical scan. This X-ray CT apparatus, following the completion of the pre-scan, directly initiates a variable helical scan toward the ending edge of the margin without forming the margin.

The variable helical scan emits X-rays while changing the helical pitch during a series of scans from the starting edge to the ending edge of the area to be imaged. The helical pitch is defined as the distance of movement in the direction of the axis of the subject to be examined while emitting X-rays once from the entire circumference. If displacement of the emitting angle changes at a particular speed, the helical pitch is the displacement speed in the slicing direction, and if the displacement speed in the slicing direction is zero, the helical pitch will be 0.

The margin refers to the X-ray emission area extending from the starting edge position of the image reconstruction to outside the reconstruction area of the image. Specifically, it refers to, in contrast to the starting edge position of the reconstruction area of the image, a particular area from the starting edge position of image reconstruction to outside of the reconstruction area of the image for the number of views required to reconstruct the image (hereinafter referred to as "BPview"). The margin is, in a conventional X-ray CT apparatus, set to ensure the emission of X-rays for the BPview to the starting edge position of the reconstruction area of the image while continuously moving the scanning position in an axis of the subject to be examined's body via a helical scan. BPview refers to the number of views required to reconstruct an image, which is the number of X-ray emissions for the predetermined angular range. This BPview depends on reconstruction methods such as the 360-degree interpolation method, the 180-degree interpolation method, the opposing beam interpolation method, the 180-degree extrapolation method, and so forth. For example, BPview is the number of views that X-rays are emitted from the angular range of 180 degrees or greater.

This X-ray CT apparatus, without forming the margin, calculates the initial helical pitch $HP_{new}$ (first helical pitch), which can ensure X-ray emission for the BPview to the starting edge position of the image reconstruction, and also controls transition timing to this initial helical pitch and predetermined helical pitch $HP_{org}$ (second helical pitch).

First, the scanning part 110, while moving the subject to be examined in the direction of the axis of the body, emits X-rays around the body axis, and then detects X-rays transmitted through the subject to be examined to obtain the transmission data. That transmission data is the data resulting from the detection of X-rays transmitted through the subject to be examined. The scan-controlling unit 122 controls the drive of this scanning part 110. More specifically, it controls the dose of X-ray radiation or the helical pitch and so forth. The image forming unit 125 pre-processes raw data obtained by detecting X-rays transmitted by the subject to be examined to form the projection data and performs a reconstruction process on this projection data to reconstruct the image of the subject to be examined. The transmission data collectively refers to this raw data and the projection data.

The CPU unit 121 is a computer in which a central processing unit (CPU), a random access memory (RAM), and a hard-disk drive (HDD) are interconnected via a bus (BUS) to enable mutual data input/output. By running a control program stored in the external storage unit, a pre-scan-determining unit 121a and a sequence-creating unit 121b are enabled.

The CPU unit 121 inputs control data into the scan-controlling unit 122. The scan-controlling unit 122, according to this control data, changes the dose of X-ray radiation or the helical pitch of the scanning part 110. The control data includes the dose of X-ray radiation emitted at the subject to be examined and the HP-distance sequence. The HP-distance sequence is the data that relates the helical pitch for the variable helical scan to the distance the bed moves at the helical pitch. The CPU unit 121, at the time of the pre-scan, inputs the control data for a pre-scan into the scan-controlling unit 122, and at the time of the variable helical scan, inputs the control data for the variable helical scan into the scan-controlling unit 122.

A pre-scan-determining unit 121a inputs the control data of the pre-scan into the scan-controlling unit 122 and monitors initiation of the variable helical scan. Then, when it reaches the timing in which the variable helical scan begins, the pre-scan-determining unit 121a inputs a trigger signal into the scan-controlling unit 122 to switch between pre-scan and scan. The pre-scan-determining unit 121a monitors flowing of the contract agent into the reconstruction area of the image. The pre-scan by the scanning part 110 allows calculation of the CT value of the image formed by the image forming unit 125. When the calculated CT value exceeds the threshold value, the trigger signal is inputted, which causes the scan-controlling unit 122 to scan via a variable helical scan. The threshold value is stored in the external storage unit in advance.

It is noted that switching between pre-scan and scan may be automatically performed by the pre-scan-determining unit 121a as a result of comparison of the CT value and the threshold value. Alternatively, it may be performed by pressing the switch button based on the displayed graph, which is shown on the monitor 124, indicating CT values of the image in chronological order. The switch button is allocated to the button designated on the input unit 123. When this switch button is pressed down, the trigger signal is input into the scan-controlling unit 122.

The sequence-creating unit 121b creates data for the HP-distance sequence and inputs it to the scan-controlling unit 122. Control data for the scan including data for this HP-distance sequence is input into the scan-controlling unit 122 prior to the pre-scan. Data for the HP-distance sequence is generated in accordance with the imaging conditions input by the input unit 123. The sequence-creating unit 121b displays the setting screen for the imaging conditions on the monitor 124 at the time of inputting imaging conditions using the input unit 123.

Figure 4:
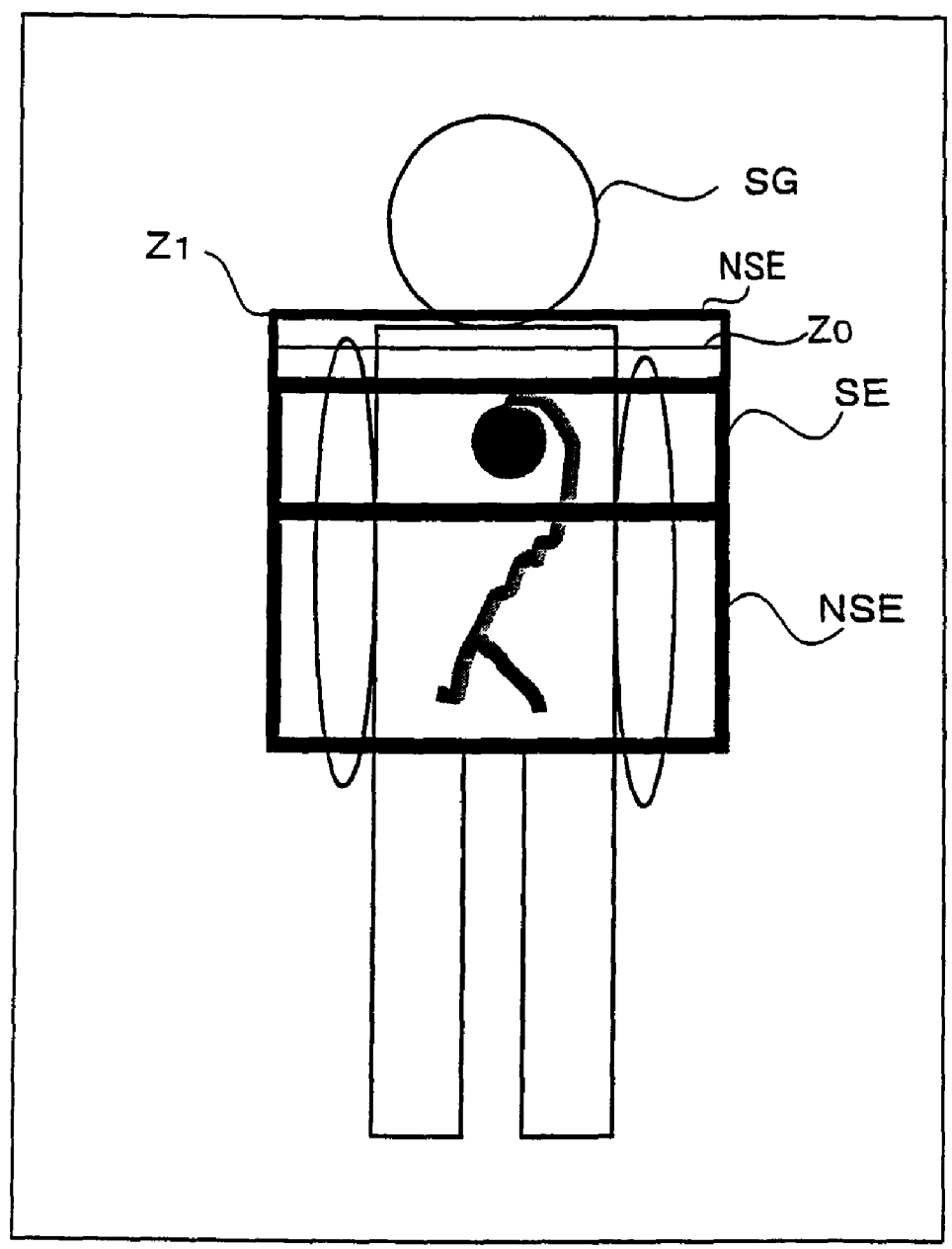
FIG. 4 is a pattern diagram that shows a screen for setting imaging conditions.

FIG. 4 is a pattern diagram that shows the setting screen of the imaging conditions. As shown in FIG. 4, the screen displays the pattern diagram (model) SG of the subject to be examined. This pattern diagram SG is a scanogram that has been imaged in advance for determining a position of slice. Using the input unit 123 and with reference to the pattern diagram SG, the operator specifies the entire reconstruction area of the image, which begins from the starting edge position $Z_1$ of the image reconstruction; the reconstruction area SE, which is reconstructed in synchronization with the biological signal among the entire reconstruction area of the image; and the reconstruction area NSE, which is reconstructed in asynchronization with the biological signal; and the pre-scan position $Z_0$ for performing the scan.

For example, the input unit 123 is used to specify the first reconstruction area of the image including the starting edge position $Z_1$ of the image reconstruction, and then the first reconstruction area of the image is specified as the reconstruction area NSE. Next, the input unit 123 is used to specify the second reconstruction area of the image that follows the first reconstruction area of the image, and then the second reconstruction area of the image is specified as the reconstruction area SE. Furthermore, the third reconstruction area of the image that follows the second reconstruction area of the image is specified, and then the third reconstruction area of the image is specified as reconstruction area NSE. The input unit 123 is again used to specify the pre-scan position $Z_0$. The sequence-creating unit 121b, reflecting the operation used in this input unit 123, displays distinctly on the monitor 124, first to third areas to reconstruct the image and the reconstruction area SE or the reconstruction area NSE of its respective areas to reconstruct the image and then displays the pre-scan position $Z_0$.

Figure 5:
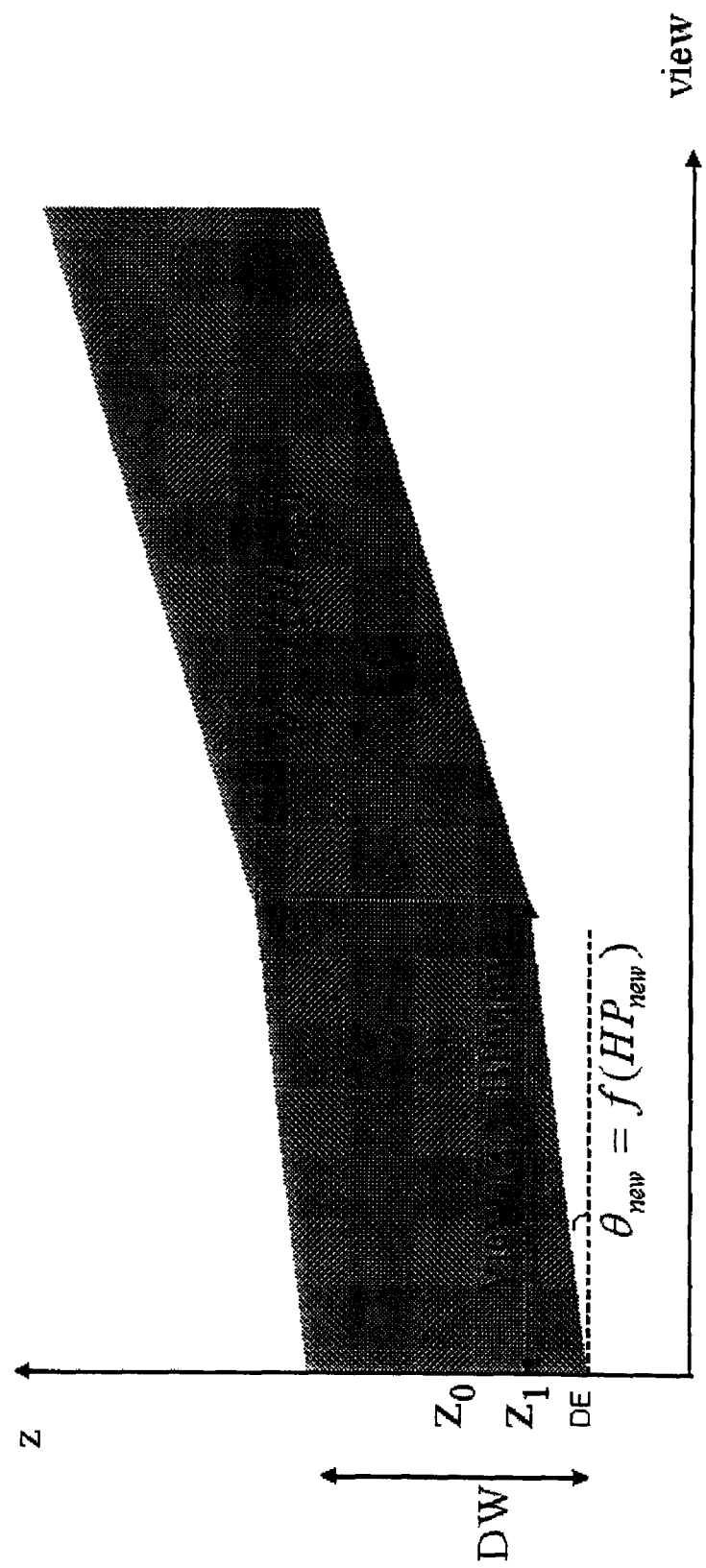
FIG. 5 shows the method of calculating the first helical pitch $HP_{new}$.

FIG. 5 shows the method of calculating the first helical pitch $HP_{new}$ via a sequence-creating unit 121b. In this figure, the vertical axis shows the position Z along the body axis, while the horizontal axis is a view. In short, FIG. 5 shows that the area along the body axis is radiated with X-rays according to the view. The sequence-creating unit 121b calculates $HP_{new}$, which enables the emission of X-rays for at least BPview to the starting edge position $Z_1$ of the image reconstruction, and the bed movement distance D at that $HP_{new}$. This calculation is based on the X-ray emission width DW for the scan, a positional relationship between the starting edge position $Z_1$ of the image reconstruction and pre-scan position $Z_0$, BPView, and the predetermined $HP_{org}$.

As shown in FIG. 5, in order to reconstruct an image of the starting edge position $Z_1$ of the image reconstruction, it is necessary for the number of views used to reconstruct the starting edge position $Z_1$ of the image reconstruction (referred to as Views ($Z_1$)) to satisfy the following (Equation 1). This is because, if X-rays cannot be emitted at the starting edge position $Z_1$ of the image reconstruction with at least the number of views of $BP_{view}$, the image of the starting edge position $Z_1$ of the image reconstruction cannot be reconstructed.

$$\text{Views}(Z_1) \geq BP\text{view} \quad \text{(Equation 1)}$$

Also, this Views ($Z_1$) can be expressed in (Equation 2) below, using the X-ray emission width DW, which is a slice width for the scan, a relative position of the starting edge position $Z_1$ of the image reconstruction to the pre-scan position $Z_0$, and the moving angle θ of the X-ray emission range. It is noted that the moving angle θ of the X-ray emission area is the slope of the X-ray emission range when the X-ray emission range, which is shown along the axis of the body, is expressed as a function of the view function.

$$\text{Views}(Z_1) = \{DW/2 - (|Z_0 - Z_1|)\}/\tan\theta \quad \text{(Equation 2)}$$

The pre-scan position $Z_0$ is generally positioned at the center of the X-ray emission range at the beginning of the scan so as to scan with a small radiation dose. Furthermore, $Z_0$–DW/2 is the edge position DE of the X-ray emission range on the side of starting edge position $Z_1$ of the image reconstruction, while $Z_1$–($Z_0$–DW/2) is the interval between the edge position DE and the starting edge position $Z_1$ of the image reconstruction. In short, DW/2–($|Z_0-Z_1|$) shows the entire amount of the interval between the edge position DE and the starting edge position $Z_1$ of the image reconstruction. Accordingly, (Equation 2) shows the Views($Z_1$) that are ensured until the edge position DE reaches the starting edge position $Z_1$ of the image reconstruction, because the X-ray emission range extends between the edge position DE at the time of initiating the scan and the starting edge position $Z_1$ of the image reconstruction at the moving angle of $\theta$.

Moreover, $\theta$ can be expressed as (Equation 3) below, as this is a function of the helical pitch HP.

$$\tan\theta = f(HP) \quad \text{(Equation 3)}$$

Therefore, (Equation 4) below is derived from the above-mentioned (Equation 1), (Equation 2), and (Equation 3).

$$f(HP) \leq \{DW/2 - (|Z_0 - Z_1|)\}/BPview \quad \text{(Equation 4)}$$

The sequence-creating unit 121b calculates DW/2–($|Z_0-Z_1|$), obtains $\{DW/2-(|Z_0-Z_1|)\}/BPview$ from a predetermined BPview, and calculates the helical pitch HP that corresponds to a maximum f (HP), which is equal to this $\{DW/2-(|Z_0-Z_1|)\}/BPview$. Then, assuming the calculated DW/2–($|Z_0-Z_1|$) as the bed movement distance D and the calculated helical pitch HP as $HP_{new}$, data of HP-distance sequence is generated.

Now, if the calculated $HP_{new}$ exceeds a predetermined $HP_{org}$, this predetermined $HP_{org}$ performs the helical scan at $HP_{org}$ from the beginning of the scan. This predetermined $HP_{org}$ is input by using the input unit 123. For this $HP_{org}$, if the reconstruction area of the image including the starting edge position $Z_1$ of the image reconstruction is the reconstruction area SE that is to be reconstructed in synchronization with the biological signal, it is $HP_{SE}$, which is input in accordance with the construction area SE or a predetermined $HP_{SE}$. If the reconstruction area of the image including the starting edge position $Z_1$ of the image reconstruction is the reconstruction area NSE to be reconstructed in synchronization with the biological signal, it is $HP_{NSE}$, which is input in accordance with the reconstruction area NSE or the predetermined $HP_{NSE}$. While the helical pitch is being changed, $HP_{new}$ and $HP_{org}$ will not be at a steady rate, as the bed accelerates its movement speed. However, for calculation of this $HP_{new}$ and the bed movement distance D, the helical pitch $HP_{org}$ after completion of the acceleration can be used, or the helical pitch $HP_{org}$ may be strictly considered while the bed is accelerating its movement speed.

Figure 6:
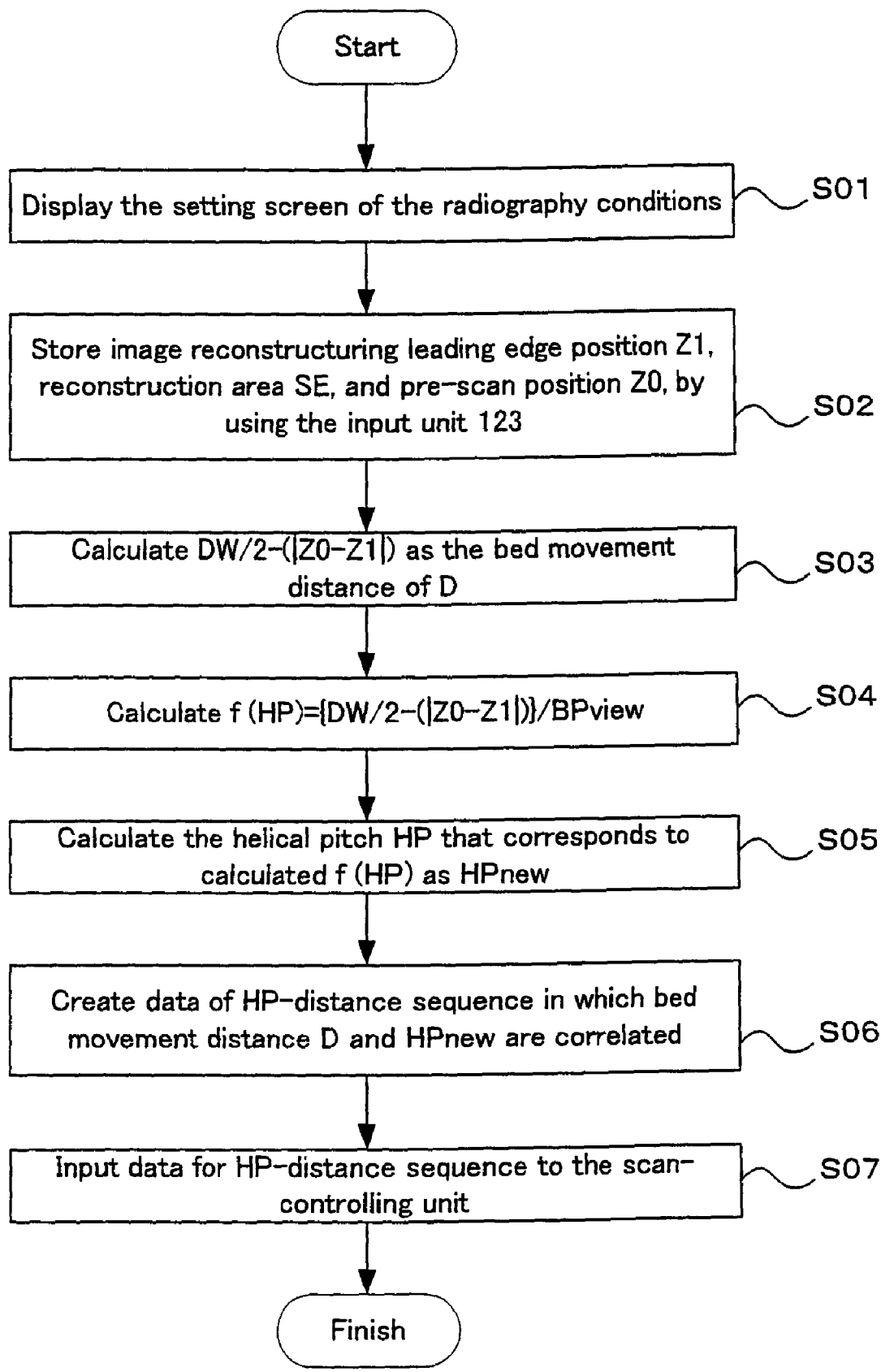
FIG. 6 shows an operation of creating data for the HP-distance sequence.

FIG. 6 shows operation of how data for the HP-distance sequence is created by this sequence-creating unit 121b. The sequence-creating unit 121b first displays, on the monitor 124, the setting screen for the imaging conditions (S01). When the operator uses the input unit 123 to input the imaging conditions, the unit stores the starting edge position $Z_1$ of the image reconstruction that is designated, the reconstruction area SE that is to be reconstructed in synchronization with the biological signal of whole reconstruction area of the image, and the pre-scan position $Z_0$ from which the pre-scan (S02) is to be performed.

When the imaging conditions are stored, the sequence-creating unit 121b calculates DW/2–($|Z_0-Z_1|$) (S03) as the bed movement distance D. The value of DW/2 is stored in the external storage unit in advance. Next, f (HP)=$\{DW/2-(|Z_0-Z_1|)\}/BPview$ is calculated (S04), and then as $HP_{new}$, helical pitch HP, which corresponds to the calculated f (HP), is calculated (S05).

When the bed movement distance D and $HP_{new}$ are calculated, data of the HP-distance sequence is created that correlates to the helical pitch of the reconstruction area SE, which is reconstructed in synchronization with the biological signal, and the distance that the bed moves at that helical pitch, the helical pitch of reconstruction area NSE that is reconstructed in asynchronization with the biological signal and the distance that the bed moves at that helical pitch, and the bed movement distance D and $HP_{new}$ (S06).

It is noted that, as to the helical pitch of the reconstruction area SE that is reconstructed in synchronization with the biological signal and its helical pitch, it is necessary to keep scanning over a multiple physical movement cycles of organs that exist in the reconstruction area SE, so it is to be set at a value less than that of the reconstruction area NSE in which image is reconstructed without synchronization with physical movement. In short, it is set to the helical pitch passing the reconstruction area SE in the period of multiple physical movement cycles.

After data for the HP-distance sequence is created, the sequence-creating unit 121b data for this HP-distance sequence is input into the scan-controlling unit 122 (S07) and the process is completed.

Figure 7:
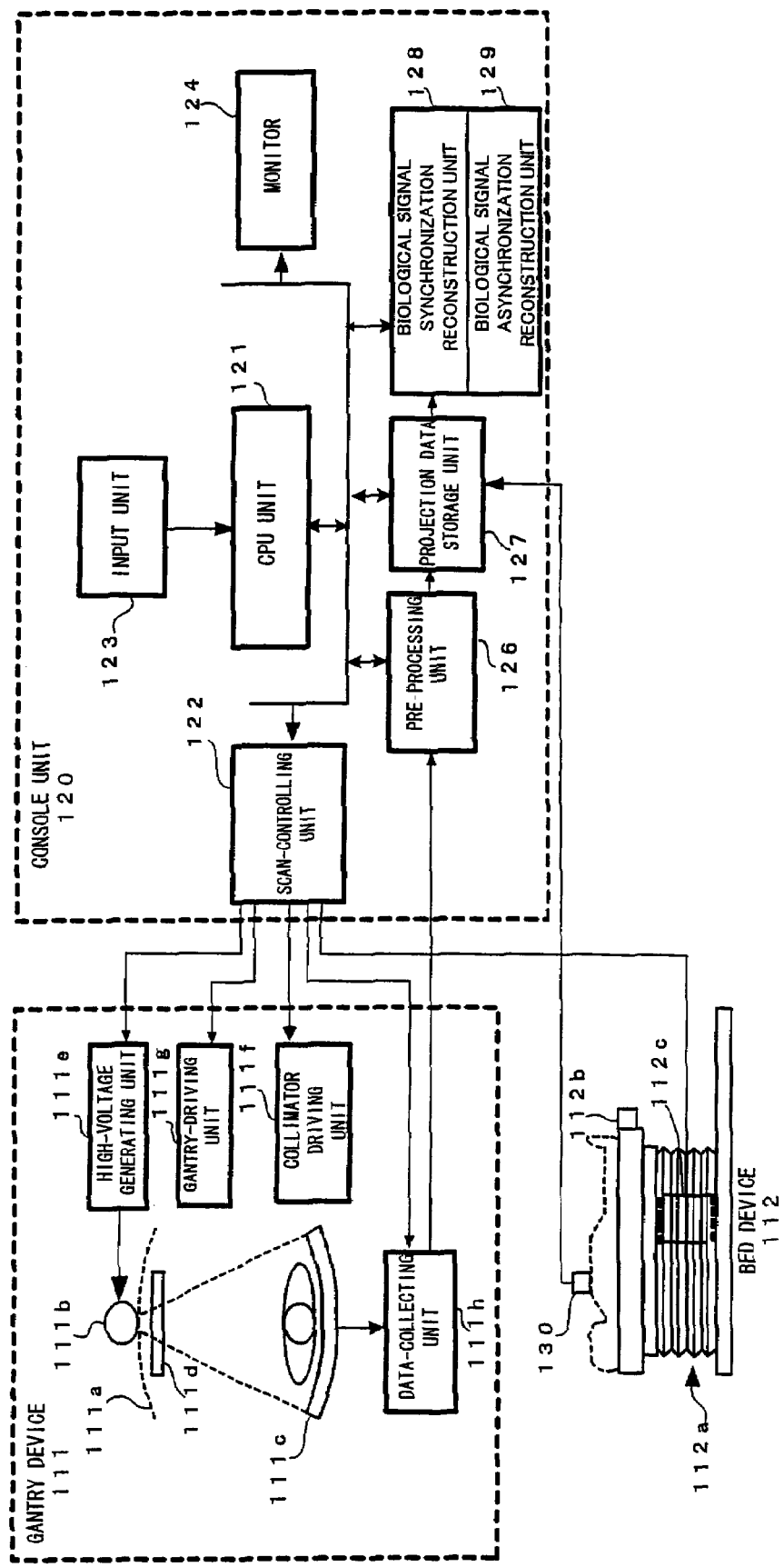
FIG. 7 is a block diagram that shows the overall structure of an X-ray CT apparatus according to the present embodiment.

FIG. 7 is a block diagram that shows the overall structure of the X-ray CT apparatus of the present embodiment. The X-ray CT apparatus includes a gantry device 111, a bed device 112, a biological signal-detecting device 130, and a console unit 120. This gantry device 111 and bed device 112 correspond to the scanning part 110.

The gantry device 111 emits X-rays, including mostly X-rays, and detects X-rays that are transmitted through a subject to be examined. This gantry device 111 has an opening into which the subject to be examined can be placed. A rotating gantry 111a is incorporated inside the gantry device 111. The rotating gantry 111a is equipped with an X-ray tube 111b and a detector 111c in opposing positions over the opening. There is a collimator 111d between the X-ray tube 111b and the detector 111c. Furthermore, a high-voltage generating unit 111e that is paired with the X-ray tube 111b is placed inside the gantry device 111, and a collimator-driving unit 111f is placed as a pair with the collimator 111d, a gantry-driving unit 111g is placed as a pair with the rotating gantry 111a, and a data-collecting unit 111h is placed as a pair with the detecting unit 113.

The rotating gantry 111a is rotated by the gantry-driving unit 111g. The rotating gantry 111a is rotated around the opening.

The X-ray tube 111b generates X-rays, supplied with a current for heating up the filament from the high voltage generating unit 111e and subjected to a high voltage. The high voltage generating unit 111e—a radio frequency inverter method, which is the method of rectifying a 50/60 Hz AC current to create a DC current—is used to convert the current to AC for a radiofrequency of at least several kHz for pressurization, and then to re-rectify and apply it.

Closing of the collimator 111d is adjusted by the collimator-driving unit 111f to form the generated X-rays into a fan beam shape or a cone beam shape. The collimator-driving unit 111f, at the time of the pre-scan for detecting the flow of the contract agent, limits closing of the collimator 111d. At the time of the variable helical scan, when the image of the subject to be examined is imaged, closing of the collimator 111d is extended. This opening of the collimator 111d uniquely determines the X-ray emission width DW. The collimator 111d is composed of a material such as tungsten that can absorb X-rays. Among X-rays that are emitted from the X-ray tube 111b, those blocked by the collimator 111d are absorbed by this collimator 111d, so only those that are not blocked by the collimator 111d are emitted at the subject to be examined.

Multi-row, multi-channel X-ray detecting elements are arranged in the detector 111c. This detector 111c detects X-rays transmitted through the subject to be examined and outputs the detected data (pure raw data) as the current signal. There is mainly an X-ray-detecting element that converts X-rays into light via a fluorescent material such as a scintillator and further into an electric charge by a photoelectric converting element such as a photo-diode, which is an indirect conversion, and the method of generating a pair of electric holes within the semiconductor by X-rays and using that transfer to an electrode as photoconduction, which is a direct conversion.

For each X-ray detecting element, the data-collecting unit 111h includes an I-V converter, an integrator, a preamplifier, and an A/D converter, which converts a current signal from each X-ray detecting element into a voltage signal, and then synchronizes the voltage signal with the cycle of X-ray emission, and integrates and amplifies this periodically to convert it into a digital signal. The data-collecting unit 111h outputs, to the console unit 120, the detected data that is converted into a digital signal.

In the bed device 112, a bed board 112b is placed on the surface of a bed base 112a. The bed board 112b is movable in the axial direction of the opening at a specified rate by a bed-driving unit 112c. The bed-driving unit 112c includes a motor in its structure and varies moving speed of the bed board 112b by controlling the current value of the driving current to the motor.

The rotation of the rotating gantry 111a and the moving of the bed board 112b are performed at the same time to make relative motion of X-ray tube 111b, the detector 111c, and the bed board 112b a helical shape, to perform a helical scan. If the rotating rate of the rotating gantry 111a is steady, the helical pitch can be changed by changing the moving speed of this bed board 112b. It is noted that, it may be possible that the bed board 112b is not moved but the gantry 111a is moved by changing the speed along the axis of the opening rotation. In addition, the pre-scan, the conventional scan or the dynamic scan is performed by rotating the rotating gantry 111a while the bed board 112b is stopped.

The biological signal-detecting device 130 detects a biological signal of a particular organ and outputs the biological signal data to the console unit 120. For example, this is composed of electrocardiographic equipment or a respiration sensor, etc. This biological signal-detecting device 130 is attached to the subject to be examined placed on the bed board 112b. The electrocardiographic equipment records time change of heart rate and then outputs an electrocardiographic data. The respiration sensor records time change of respiration and then outputs respiration data that shows time change of the lung.

The console unit 120 includes a scan-controlling unit 122, a pre-processing unit 126, a projection data storage unit 127, a biological signal synchronization reconstruction unit 128, a biological signal asynchronization reconstruction unit 129, a CPU unit 121, a monitor 124, and an input unit 123.

The external storage unit 1c of the CPU unit 121 stores control program of X-ray CT apparatus. This control program is appropriately arranged in the main storage unit 1b. The central processing unit 1a, by using the main storage unit 1b as a workarea, interprets and performs this program and controls integration of X-ray CT apparatus.

This CPU unit 121 allows a pre-scan-determining unit 121a and a sequence-creating unit 121b to work. Also, the CPU unit 121, in reconstructing a volume image, segments the obtained projection data into an area reconstructed in synchronization with the body and an area reconstructed in asynchronization with the body, controls the biological signal synchronization reconstruction unit 128 and the biological signal asynchronization reconstruction unit 129 to conduct a different reconstruction method to each projection data for image reconstruction. In order to combine this image, images to be combined are partly superimposed to reconstruct the image, and also a feathering process is performed at the border of the image.

The scan-controlling unit 122, by the use of the trigger signal input by the CPU unit 121, is shifted from the pre-scan to that of the scan using the variable helical scan, and according to the control data including the data for the HP-distance sequence created by the CPU unit 121, outputs a driving signal to a high voltage generating unit 111e, a gantry-driving unit 111g, a data-collecting unit 111h, a collimator-driving unit 111f, and a bed-driving unit 112c. By outputting a driving signal to the gantry-driving unit 111g and the bed-driving unit 112c, a helical scan is performed by a relative motion in a helical way of X-ray tube 111b and the detector 111c toward the bed board 112b. Also, moving speed of the bed board 112b is varied to perform a helical scan at the helical pitch in accordance with the HP-distance sequence.

The scan-controlling unit 122, during the pre-scan, does not output the driving signal into the bed-driving unit 112c. When the trigger signal is input from the CPU unit 121, the driving signal is output to the bed-driving unit 112c to start moving the bed board 112b. At the beginning of the scan, driving signal of the current value that achieves the helical pitch $HP_{new}$ included in the HP-distance sequence is transmitted to the bed-driving unit 112c, until the bed board 112b is moved by the bed movement distance D that is also included in the HP-distance sequence, and X-rays is emitted at the starting edge position $Z_1$ of the image reconstruction for the amount that corresponds to BPview. When the bed board 112b is moved by the bed movement distance D from the beginning of the scan, driving signal of the current value that achieves the helical pitch $HP_{org}$ included in the HP-distance sequence is transmitted to the bed-driving unit 112c.

In the case of the reconstruction area NSE that is reconstructed in asynchronizing the scan position with the biological signal, driving signal of the current value that achieves the helical pitch $HP_{NSE}$ of its reconstruction area NSE as $HP_{org}$ is transmitted to the bed-driving unit 112c. In case of the reconstruction area SE that is reconstructed with the scan position synchronized with the biological signal, driving signal of the current value that achieves the helical pitch $HP_{SE}$ of its reconstruction area SE as $HP_{org}$ is transmitted to the bed-driving unit 112c.

The image forming unit 125 includes a pre-processing unit 126, a projection data storage unit 127, a biological signal synchronization reconstruction unit 128, and a biological signal asynchronization reconstruction unit 129.

The pre-processing unit 126 conducts sensitivity correction that corrects the strength of X-rays to the pure raw data, and outputs the projection data to the projection data storage unit 127. The projection data output by the pre-processing unit 126 is stored in the projection data storage unit 127. Also, the biological signal data output by the biological signal-detecting device 130 is also stored in the projection data storage unit 127. The projection data and biological signal data are stored, in chronological order that each data element is generated.

The biological signal synchronization reconstruction unit 128, from the projection data and the biological signal data that correspond to the reconstruction area SE that reconstruct the image in synchronization with the biological signal for the scan, reconstructs a volume image via the biological signal synchronization reconstruction method.

The biological signal asynchronization reconstruction unit 129 reconstructs the volume image from the projection data that corresponds to the reconstruction area NSE that reconstructs the image in asynchronization with the biological signal. Also, biological signal asynchronization reconstruction unit 129 reconstructs the image inside the subject to be examined from the projection data obtained by the pre-scan, inputs it to the pre-scan-determining unit 121a.

The volume image reconstructed in accordance with the variable helical scan is combined and processed by feathering process by the CPU unit 121, and then displayed on the monitor 124.

Figure 8:
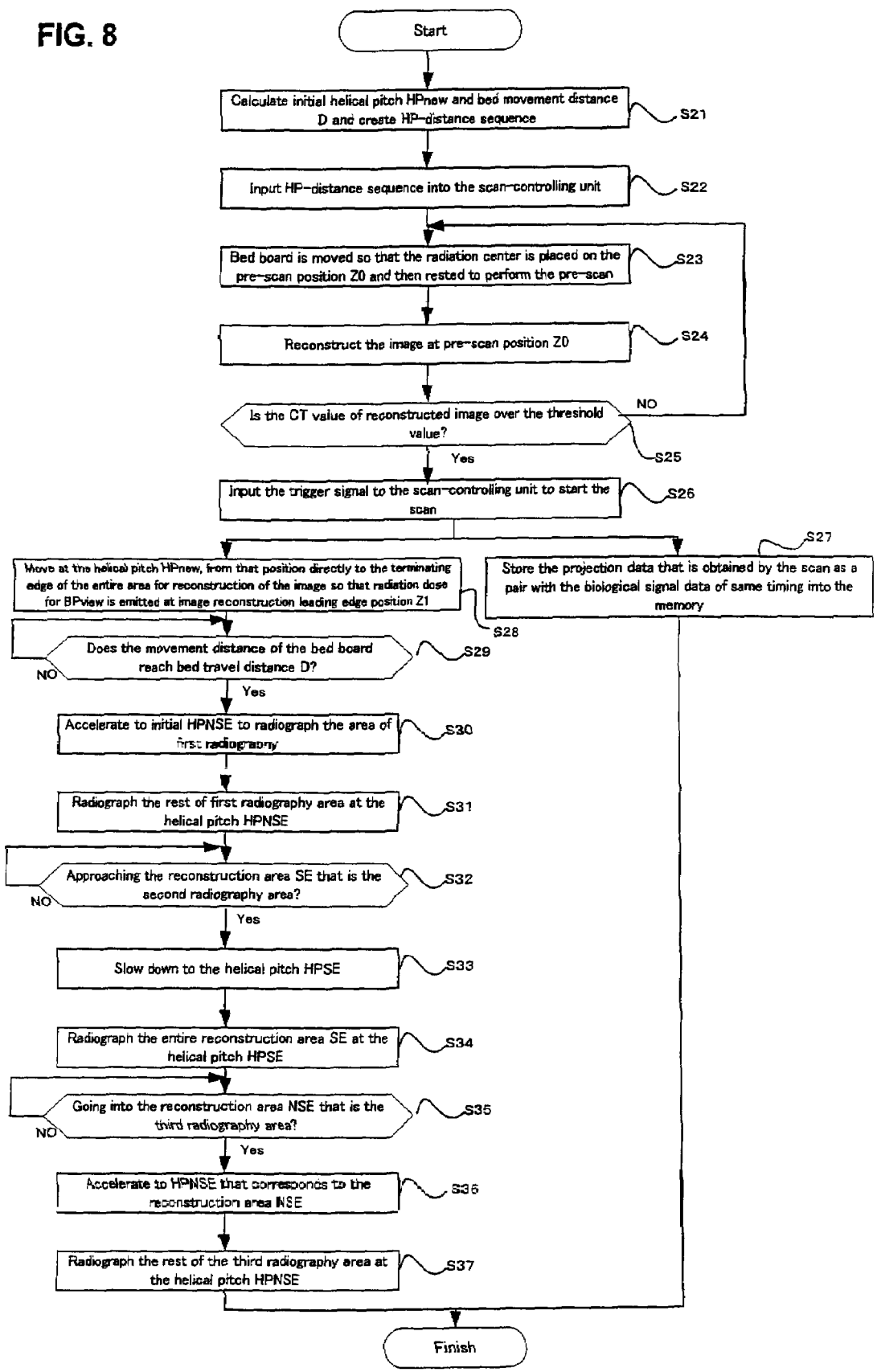
FIG. 8 is a flowchart that shows how projection data is obtained in accordance with the HP-distance sequence of the X-ray CT apparatus.
Figure 9:
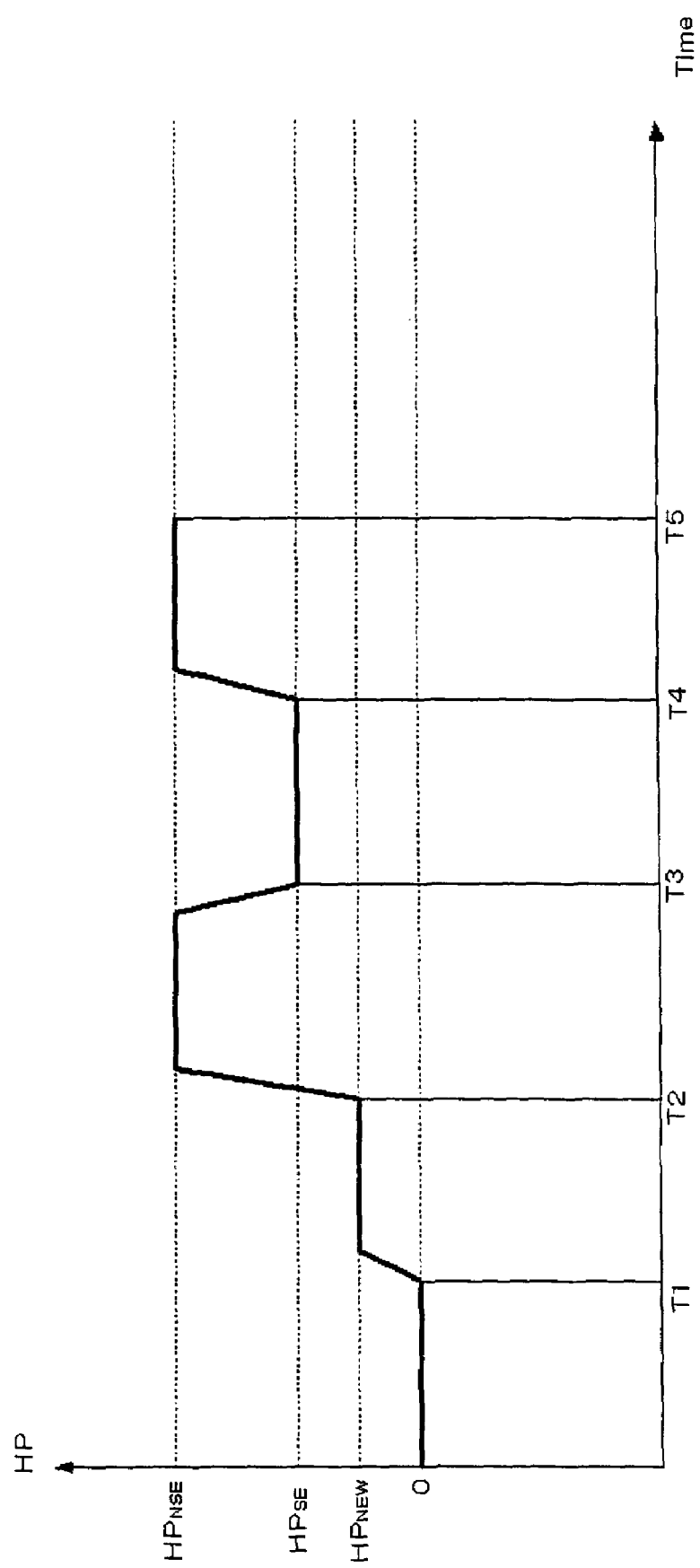
FIG. 9 is a graph that shows the helical pitch for the overall reconstruction area of the image.

FIG. 8 is a flow chart how the projection data is obtained in accordance with the HP-distance sequence of this X-ray CT apparatus. Also, FIG. 9 is a graph showing the helical pitch in the entire reconstruction area of the image. Its vertical axis shows the helical pitch, while its horizontal axis shows the time. Now, within the whole area of imaging, the reconstruction area NSE that is reconstructed in asynchronization with the body is set in the first reconstruction area of the image including the starting edge position $Z_1$ of the image reconstruction, the reconstruction area SE that is reconstructed in synchronization with the biological signal is set in the second reconstruction area of the image including the heart position that follows the second reconstruction area of the image, and the reconstruction area NSE that is reconstructed in asynchronization with the body is set in the third reconstruction area of the image including the imaging ending edge position that follows the second reconstruction area of the image.

Firstly, the sequence-creating unit 121b, once the pre-scan position $Z_0$ and the starting edge position $Z_1$ of the image reconstruction is input, calculates the initial helical pitch $HP_{new}$ and the bed movement distance D, creates the HP-distance sequence (S21), and inputs it to the scan-controlling unit 122 (S22).

The bed board 112b is moved and then comes to rest on the pre-scan position $Z_0$, by the scan-controlling unit 122, so that X-ray tube 111b is positioned, and the opening of the collimator 111d is limited by the pre-scan and then the pre-scan is performed (S23). During this pre-scan, the biological signal asynchronization reconstruction unit 129 reconstructs the projection data to reconstruct the image for the pre-scan position $Z_0$ (S24).

The pre-scan-determining unit 121a compares the CT value of the image reconstructed by the biological signal asynchronization reconstruction unit 129 and the predetermined threshold value (S25), and if such CT value is more than the threshold value (S25, Yes), it inputs the trigger signal that causes the scan-controlling unit 122 to start the scan to start the scan (S26). Until the CT value exceeds the threshold value, comparison from the pre-scan (S23) and comparison from the CT value and the threshold value (S25) are repeated.

As shown in FIG. 9, depending on the process of controlling, for the period of this S23 to S26, which is from the time of starting the pre-scan till the time when the contract agent is flown into the reconstruction area of the image (T1zone), the helical pitch remains 0.

As soon as the scan is initiated, the biological signal data TD that is output by the biological signal-detecting device 130 as the time passes is stored in the storage area as a pair with the projection data PD that is created during the same period (S27).

Meanwhile, when the scan is initiated, the bed board 112b that has been placed so that the pre-scan position $Z_0$ is positioned at the center of the emission of X-rays is moved directly toward the ending edge of the reconstruction area of the image from that position.

The bed board 112b that has been placed, at the time of starting the scan, so that the pre-scan position $Z_0$ is positioned at the center of X-rays emission is moved directly toward the ending edge of the entire reconstruction area of the image starting edge position $Z_1$ of the image reconstruction from that position so as to emit X-rays for the BPview at the helical pitch $HP_{new}$ (S28). When the movement distance of the bed board 112b reaches the bed movement distance D (S29, Yes), the helical pitch is accelerated to the original $HP_{NSE}$ to image the first reconstruction area of the image (S30), and then images the rest of the first reconstruction area of the image at the helical pitch $HP_{NSE}$ (S31). It is noted that, the scan position is determined by the position detection or sequence control of the sensor of the bed board 112b.

As shown in FIG. 9, depending on this process of controlling, for the period that the movement distance of the bed board 112b reaches the bed movement distance D (T2zone), the helical scan is performed at the helical pitch $HP_{new}$. Also, depending on this process of controlling, for the time period from the time the movement distance of the bed board 112b reaches the bed movement distance D just before going into the second reconstruction area of the image (T3zone), the helical scan is performed at the initial $HP_{NSE}$.

It is noted that, while accelerating from the helical pitch 0 to the helical pitch $HP_{new}$, and also accelerating from the helical pitch $HP_{new}$ to the helical pitch $HP_{NSE}$, the projection data is obtained as usual, and the projection data obtained during that period is also used as the data to reconstruct.

As the reconstruction area SE that is the second reconstruction area of the image approaches (S32, Yes), for the reconstruction area SE, it slows down to the helical pitch $HP_{SE}$ that enables scanning (S33) over multiple cycles of changing the biological signals from the helical pitch $HP_{NSE}$. The whole reconstruction area SE is imaged at this helical pitch $HP_{SE}$ (S34). When it passes the reconstruction area SE and then goes into the reconstruction area NSE that is the third reconstruction area of the image (S35, Yes), it is accelerated to $HP_{NSE}$ that corresponds to the reconstruction area NSE (S36), and the rest of the third reconstruction area of the image is obtained at the helical pitch $HP_{NSE}$ (S37).

As shown in FIG. 9, depending on this process of controlling, as the reconstruction area SE that is the second reconstruction area of the image (T3 zone ending edge) approaches, the helical pitch slows down to $HP_{SE}$. Until the second reconstruction area of the image is imaged (T4zone), the helical scan is performed at the helical pitch $HP_{SE}$. Furthermore, depending this process of controlling, as the reconstruction area NSE of the third reconstruction area of the image is reached, it accelerates to the helical pitch $HP_{NSE}$, and until the third reconstruction area of the image is imaged (T5zone), the helical scan is performed at this helical pitch $HP_{NSE}$.

In this way, for this X-ray CT apparatus, it is arranged to calculate the helical pitch $HP_{New}$ that is still possible to emit X-rays for BPview to the starting edge position $Z_1$ of the image reconstruction even if the bed board 112b is moved directly toward the ending edge of reconstruction area of the image after the pre-scan, and to perform the helical scan at this helical pitch $HP_{new}$ at the initial period of the scan until the bed board 112b moves by the amount of the bed movement distance D. So the margin is not needed to be set outside the reconstruction area of the image to obtain an image of the starting edge position $Z_1$ of the image reconstruction, preventing the unnecessary risk of being exposed to radiation. Also, there is no need to move the bed board 112b backward once to set a margin outside the reconstruction area of the image, so it is possible to start the scan immediately after the pre-scan, which means, just after detecting the flow of the contract agent, the scan can be initiated quickly and also a high-resolution image can be reconstructed with the benefit of the contract effects by the contract agent.

It is noted that, if X-rays is emitted at the initial helical pitch $HP_{org}$, instead of X-ray emitting for the entire BPview to the starting edge position $Z_1$ of the image reconstruction at the helical pitch $HP_{New}$, the amount that is short to reconstruct the image may be covered by maximum helical pitch $HP_{New}$ to compensate for it. In order to calculate the helical pitch $HP_{New}$, the amount that is short to reconstruct the image when X-rays is emitted at initial helical pitch $HP_{org}$ and the maximum helical pitch $HP_{New}$ may be considered.

Embodiment to Obtain the Projection Data 2

Next, a second embodiment to obtain the projection data is explained. The X-ray CT apparatus according to this second embodiment, without setting a margin, so as to ensure the number of X-ray emissions for the number of views required to reconstruct the image of the starting edge position of the image reconstruction to the starting edge position $Z_1$ of image reconstruction, the number of views for the scan at helical pitch 0 toward the starting edge position $Z_1$ of the image reconstruction is calculated, and after this number of views has been imaged by the conventional scan, it is changed to predetermined helical pitch $HP_{org}$. In short, while the first embodiment changes the pitch from $HP_{new}$ to $HP_{org}$, the second embodiment changes the helical pitch from 0 to $HP_{org}$. The scanning time by the conventional scan is the time to compensate for the number of views that is short for the BPview emitting to the starting edge position $Z_1$ of the image reconstruction when X-rays emission is initiated at $HP_{org}$.

Figure 10:
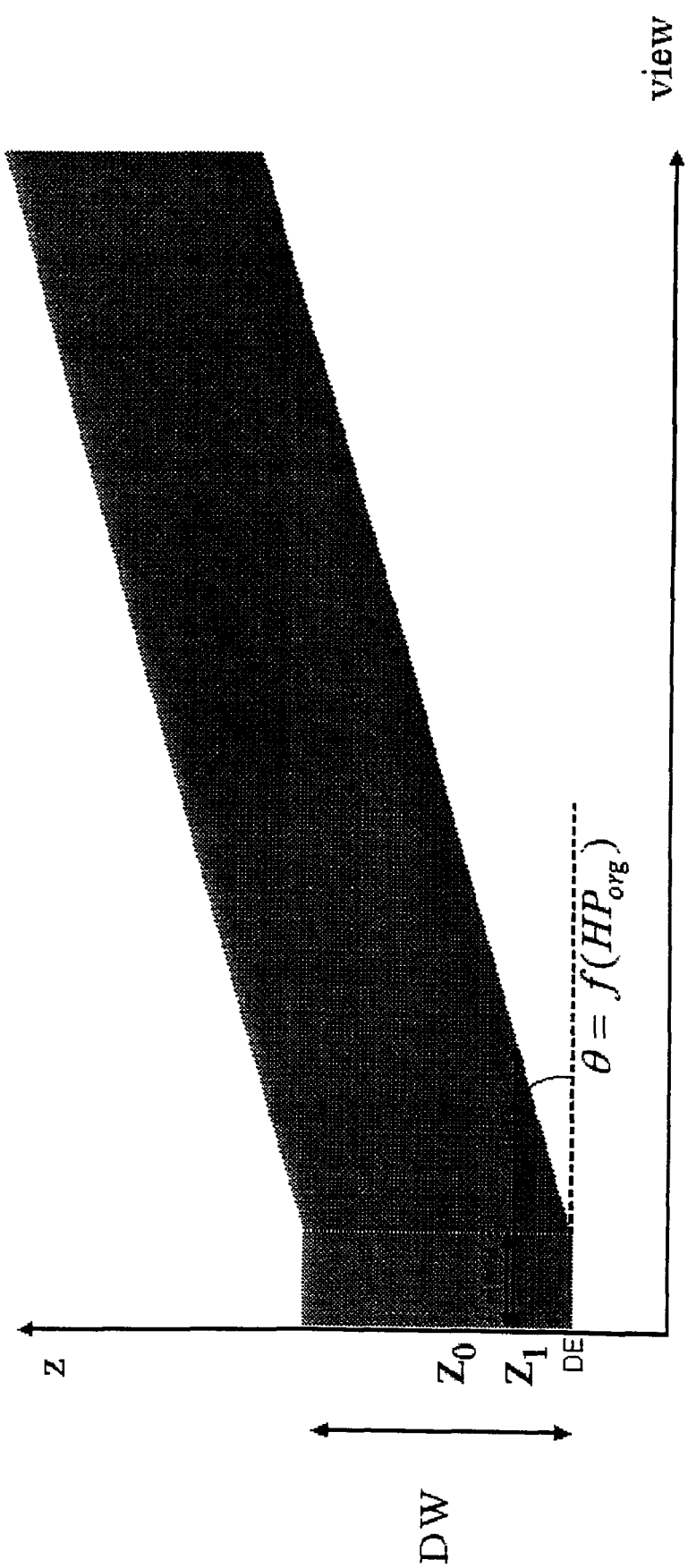
FIG. 10 shows the method of calculating the number of views for a variable helical scan with a helical pitch value of 0.

FIG. 10 shows the calculating method for the number of views performing the variable helical scan at the helical pitch 0 by the sequence-creating unit 121b. In this figure, the vertical axis shows the position Z in the direction of body axis direction, horizontal axis a view and the area of body axis direction in which X-rays is emitted according to the view. It is similar to the first embodiment in that, in order to reconstruct the image of the starting edge position $Z_1$ of the image reconstruction, the number of views Views ($Z_1$) that is used to reconstruct the starting edge position $Z_1$ of the image reconstruction must satisfy above-mentioned Equation 1. Now, if, of such numbers of views Views ($Z_1$), the number of views that can be imaged by the conventional scan is assumed to be Cviews ($Z_1$), above Equation 2 can be expressed in (Equation 2') below.

$$\text{Views}(Z_1) = \{DW/2 - (|Z_0 - Z_1|)\}/\tan\theta + C\text{views}(Z_1) \quad \text{(Equation 2')}$$

Also, this θ is uniquely identified by the predetermined helical pitch $HP_{org}$, and above-mentioned Equation 3 can be also expressed in (Equation 3') below.

$$\tan\theta = f(HP_{org}) \quad \text{(Equation 3')}$$

Therefore, above (Equation 1), (Equation 2'), and (Equation 3') derives (Equation 4') below.

$$C\text{views}(Z_1) \geqq BP\text{view} - \{DW/2 - (|Z_0 - Z_1|)\}/\tan f(HP_{org}) \quad \text{(Equation 4')}$$

The sequence-creating unit 121b calculates, as Cviews ($Z_1$), BPview−$\{DW/2-(|Z_0-Z_1|)\}/\tan f(HP_{org})$, and generates the data of the HP-distance sequence calculated Cviews ($Z_1$) is related to the helical pitch 0. Now, If BPview ≦ $\{DW/2-(|Z_0-Z_1|)\}/\tan f(HP_{org})$, the conventional scan will not be performed in principle.

Figure 11:
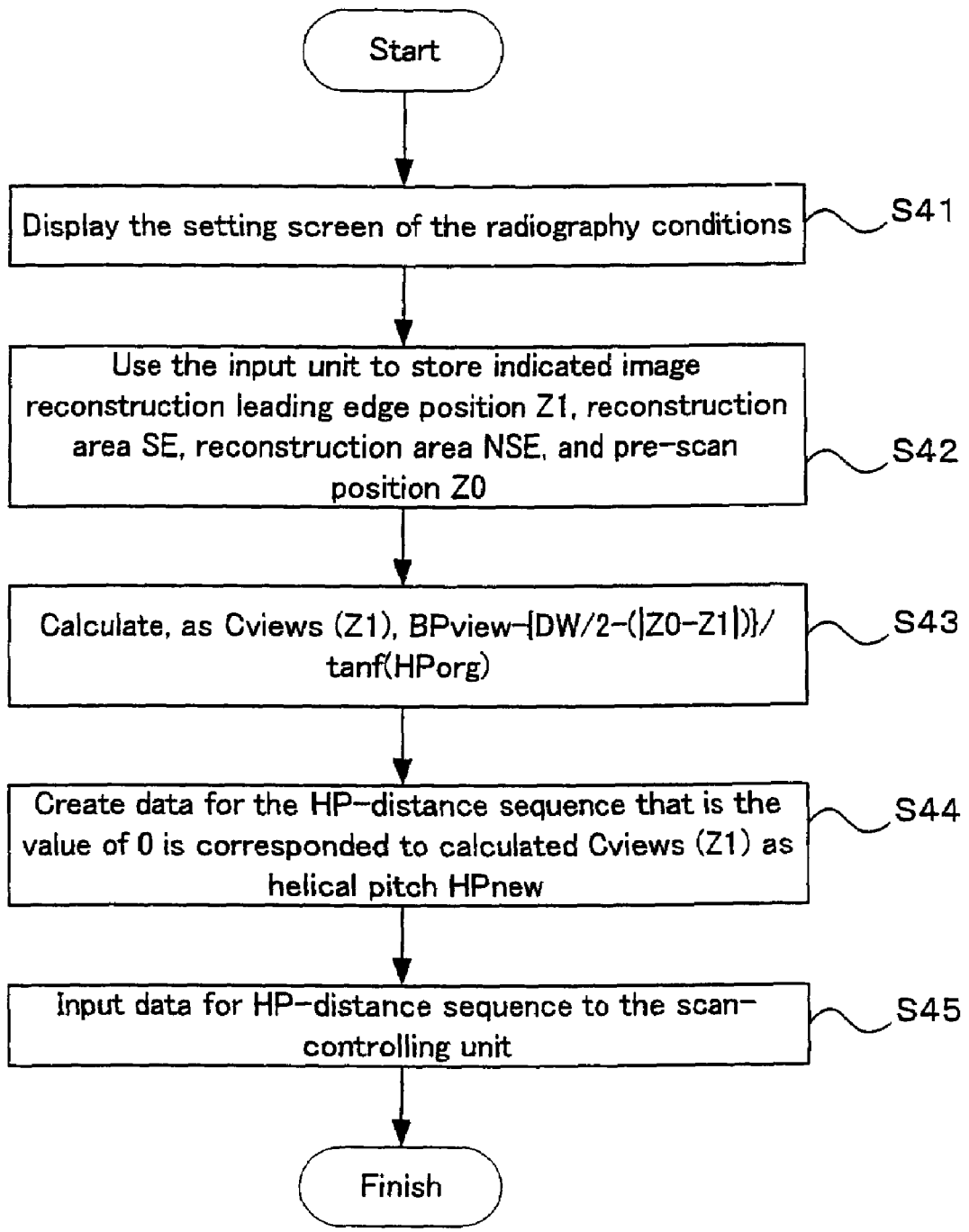
FIG. 11 shows how the scan area is created for a helical scan with a pitch value of 0.

FIG. 11 shows an operation of how the part that was scanned by the helical scan at the pitch of 0 is generated, among the data-generating operations for the HP-distance sequence by the sequence-creating unit 121b. Firstly, the sequence-creating unit 121b displays the setting screen on the monitor 124 (S41). When the operator inputs the imaging conditions using the input unit 123, the starting edge position $Z_1$ of indicated image reconstruction, of the whole reconstruction area of the image, the reconstruction area SE reconstructed in synchronization with the biological signal, the reconstruction area NSE that is reconstructed in asynchronization with the biological signal, and the pre-scan position $Z_0$ that performs the pre-scan are stored (S42).

Storing these imaging conditions, the sequence-creating unit 121b, as Cviews($Z_1$), calculates BPview−$\{DW/2-(|Z_0-Z_1|)\}/\tan f(HP_{org})$ (S43). The value of DW/2 is stored in the external storage unit in advance. When Cviews ($Z_1$) is calculated, the data for the HP-distance sequence in which the value of 0 is corresponded to this calculated Cviews ($Z_1$) as a helical pitch $HP_{new}$ is stored (S44).

When the HP-distance sequence data is generated, the sequence-creating unit 121b inputs this HP-distance sequence data into the scan-controlling unit 122 (S45), and the process is completed.

Figure 12:
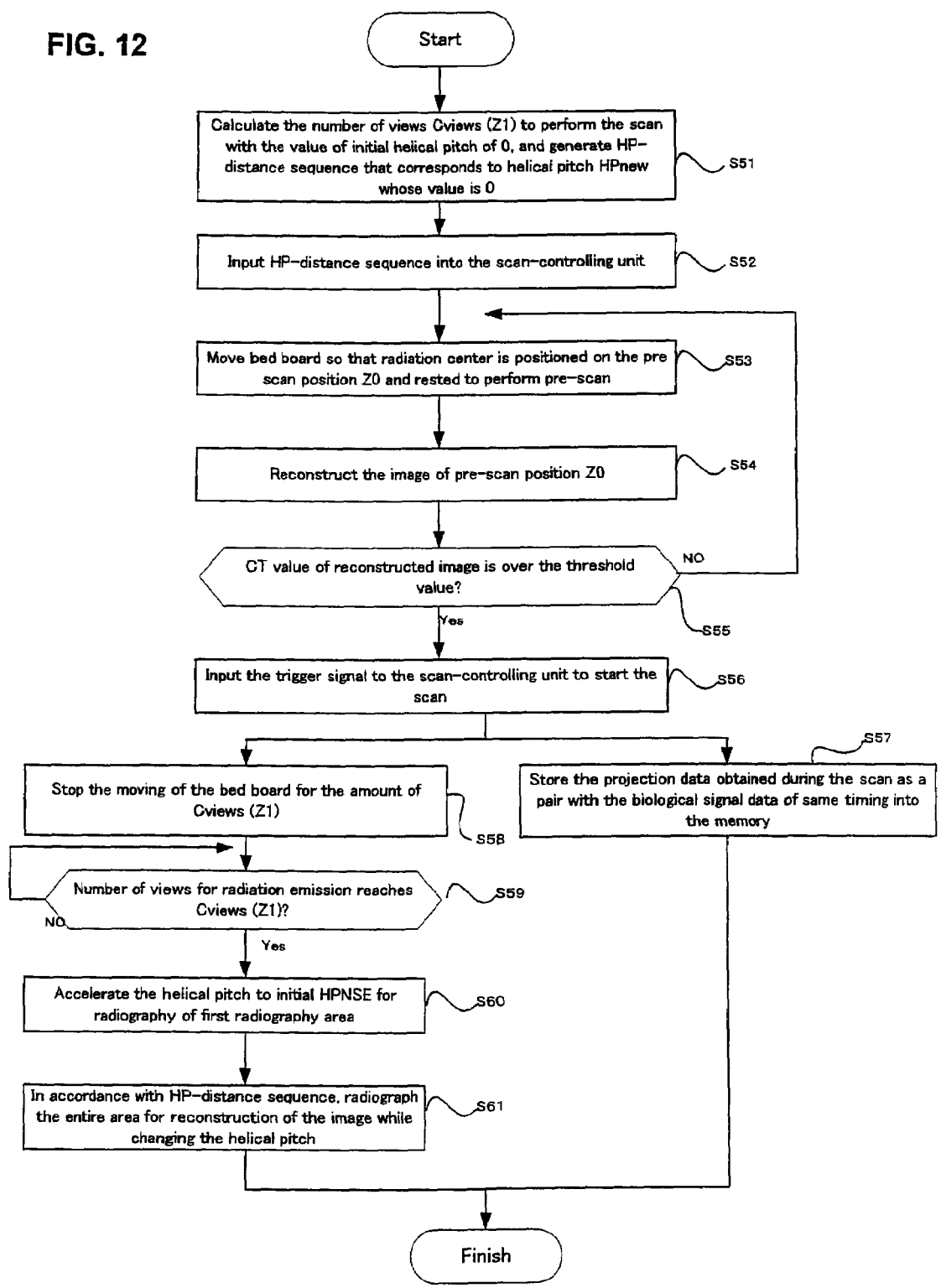
FIG. 12 is a flowchart that shows the initial operations of obtaining projection data, including a first helical pitch of 0 in accordance with the HP-distance sequence.
Figure 13:
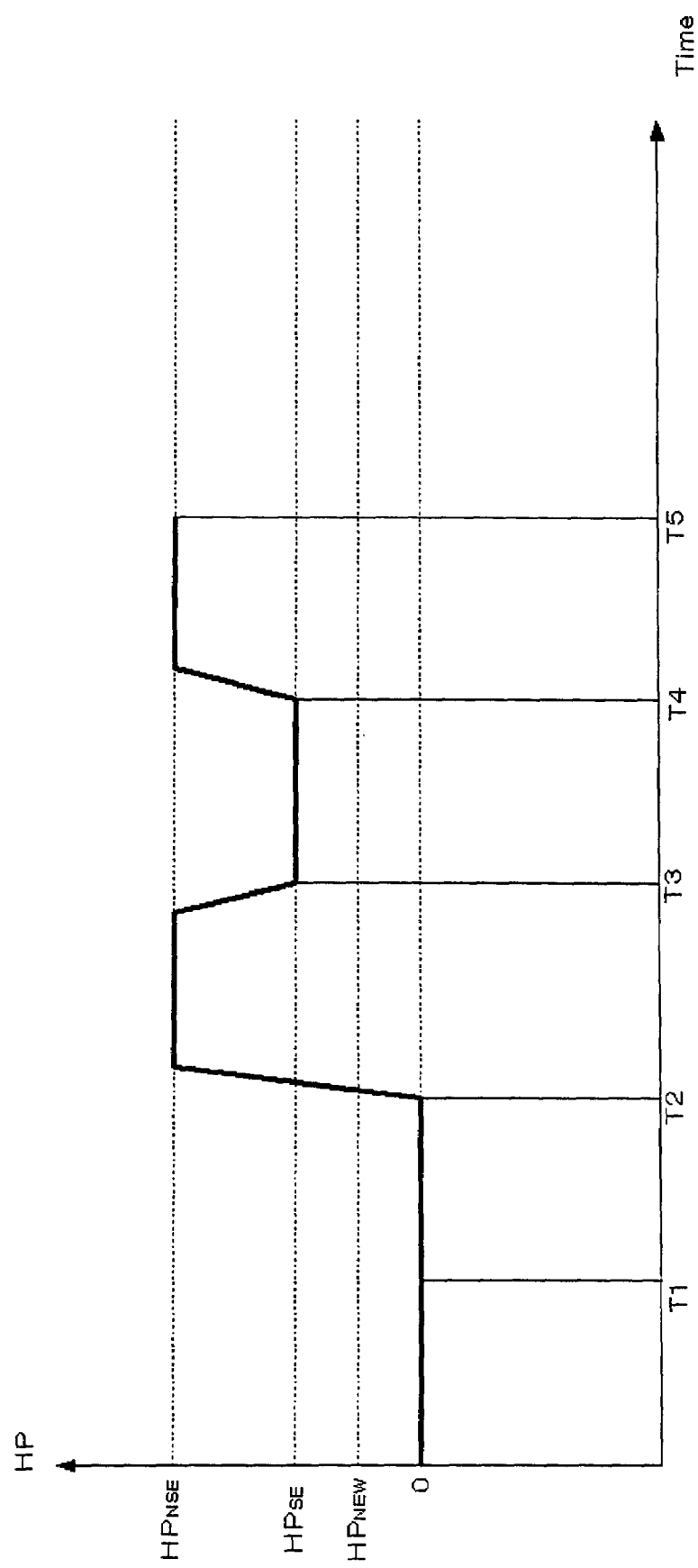
FIG. 13 is a graph that shows the helical pitch for initial operations. The vertical axis thereof shows the helical pitch, and the horizontal axis shows the time.

FIG. 12 is a flow chart that shows the initial movement, of the operation of obtaining the projection data in accordance with the HP-distance sequence of this X-ray CT apparatus. Also, FIG. 13 is a graph showing the helical pitch for that initial movement. Its vertical axis shows the helical pitch, while the horizontal axis shows the time. Now, within the entire imaging area, the reconstruction area NSE that is reconstructed in asynchronization with the body is set in the first reconstruction area of the image including the starting edge position $Z_1$ of the image reconstruction, and the reconstruction area SE that is reconstructed in synchronization with the biological signal is set in the second reconstruction area of the image including the heart position that follows the second reconstruction area of the image, and the reconstruction area NSE that is reconstructed in asynchronization with the body is set in third reconstruction area of the image including the imaging ending edge position that follows the second reconstruction area of the image.

Firstly, the sequence-creating unit 121b, when the pre-scan position $Z_0$ and the starting edge position $Z_1$ of the image reconstruction are input, calculates the number of views Cviews ($Z_1$) that performs the scan at the initial helical pitch of 0, creates the HP-distance sequence that is correlated with the helical pitch $HP_{new}$ whose value is 0 (S51), and then inputs it into the scan-controlling unit 122 (S52).

By the scan-controlling unit 122, the bed board 112b is moved and comes to rest so that X-ray tube 111b is positioned on the pre-scan position $Z_0$, and also the opening of the collimator 111d is limited due to the pre-scan to perform the pre-scan (S53). During this pre-scan, biological signal asynchronization reconstruction unit 129 reconstructs the projection data to reconstruct the image inside the subject to be examined (S54).

The pre-scan-determining unit 121a compares the CT value of the image reconstructed by the biological signal asynchronization reconstruction unit 129 and predetermined threshold value (S55), and if the CT value is more than the threshold value (S55, Yes), a trigger signal is input into the scan-controlling unit 122 to start the scan (S56). Until the CT value exceeds the threshold value, comparison from the pre-scan (S53) to the comparison between the CT value and the threshold value (S55) are repeated.

As shown in FIG. 13, depending on the process of controlling, for the period of this S53 to S56, that is from the time of starting the pre-scan to the time that the contract agent is flown into the reconstruction area of the image (T1zone), the helical pitch remains 0.

As soon as the scan is initiated, the biological signal-detecting device 130 stores the biological signal data TD that is output as the time passes stores as a pair with the projection data PD that is created at the same time into the storage area (S57).

At the scan starting position, for the amount of Cviews ($Z_1$), motion of the bed board 112b is stopped (S58). In short, while X-rays is emitted for the amount of Cviews ($Z_1$), helical $HP_{new}$ with the value of "0" is set. When the number of views for the X-RAY emission reaches Cviews ($Z_1$) (S59, Yes), the helical pitch is accelerated to the initial $HP_{NSE}$ to image the first reconstruction area of the image (S60), and thereafter, while changing the helical pitch in accordance with the HP-distance sequence, the overall reconstruction area of the image is obtained (S61).

As shown in FIG. 13, depending this process of controlling, for the period that X-rays is emitted for the amount of Cviews ($Z_1$) only after shifting from the pre-scan to the scan (T2zone), the scan is performed at the helical pitch $HP_{new}$ with the value of "0" that is substantially as the conventional scan. When X-rays emission reaches Cviews ($Z_1$), until the helical pitch is accelerated to $HP_{NSE}$, and the first reconstruction area of the image is imaged (T3zone), the helical scan is performed at the initial pitch of $HP_{NSE}$.

It is noted that, even while accelerating from the helical pitch 0 to the helical pitch HPNSE, the projection data is still obtained, and the projection data obtained during that period is used as a data to reconstruct.

In this way, in order to obtain the image of the starting edge position $Z_1$ of the image reconstruction, even X-ray CT apparatus according to this second embodiment is not needed to set a margin outside the reconstruction area of the image, eliminating unnecessary risk of being exposed to radiation. Also, there is no need to move the bed board 112b backward to set a margin outside the reconstruction area of the image, and the scan can be initiated immediately after the pre-scan, so once the flow of the contract agent is detected, the scan can be initiated quickly, high-resolution image with the benefit of the contract effect by the contract agent can be reconstructed.

Reconstruction Process

Figure 14:
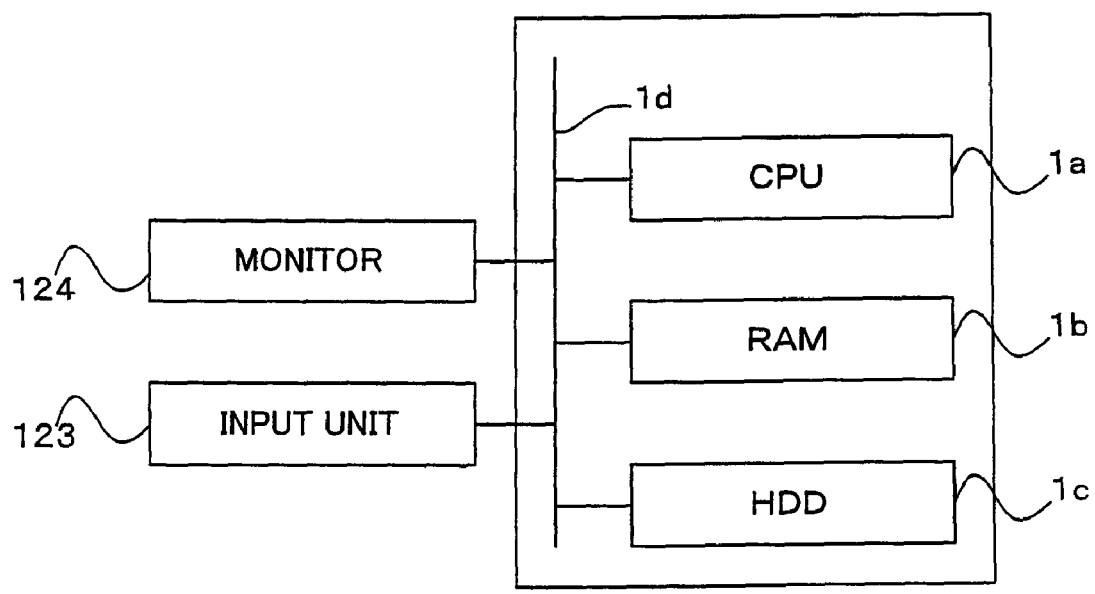
FIG. 14 is a block diagram that shows the structure of the image reconstruction processing apparatus, which is an embodiment of the image reconstruction processing technology according to the present embodiment.

FIG. 14 is a block diagram showing the image reconstruction processing apparatus for an embodiment of image reconstruction processing technology according to the present embodiment. As shown in FIG. 14, the image reconstruction processing apparatus is a computer that interconnects a central processing unit (CPU) 1a, a main storage unit (RAM) 1b, and an external storage unit (HDD) 1c via the bus 1d so that mutual data input/output is possible. The bus 1d has a monitor 124 and an input unit 123 connected to each other via a controller which is not shown in the figure. The monitor 124 is a display device such as a CRT and a liquid-crystal display, and the input unit 123 is an input interface device such as a keyboard, a mouse, or a trackball, etc.

In the external storage unit 1c, the operating system (OS) of the image reconstruction processing apparatus and the program of the image reconstruction process are stored, and the program is appropriately arranged to the main storage unit 1b. The central processing unit 1a interprets and runs the program arranged in the main storage unit 1b, data-processes using the main storage unit 1b as a workarea, and controls display of the monitor 124.

By running the program by this central processing unit 1a, the image reconstruction processing apparatus reconstructs the volume image from the projection data to display it on the monitor 124. For reconstruction of the volume image, the projection data is segmented and a different reconstruction method is applied to each of them to make a combined display.

This image reconstruction processing apparatus may be a CPU unit 121 of X-ray CT apparatus, workstation or a computer like a PC.

Figure 15:
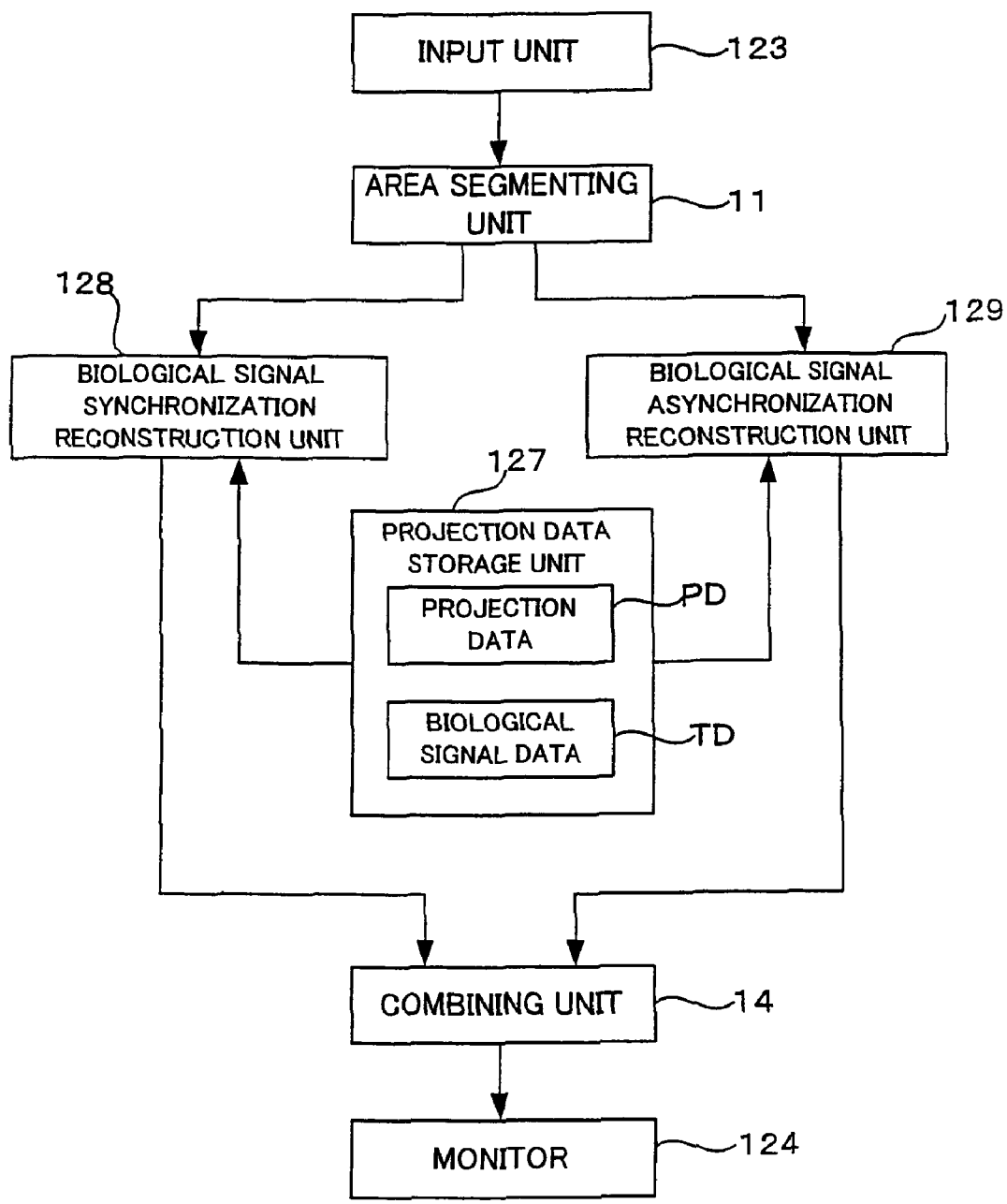
FIG. 15 is a block diagram that shows the functions of this image reconstruction processing apparatus.

FIG. 15 is a block diagram showing functions of this image reconstruction processing apparatus. As shown in FIG. 15, the image reconstruction processing apparatus has a projection data storage unit 127, an area segmenting unit 11, a biological signal synchronization reconstruction unit 128, a biological signal asynchronization reconstruction unit 129, and a combining unit 14.

The projection data storage unit 127 includes an external storage unit 1c in its structure. The projection data PD and the biological signal data TD that are obtained by X-ray CT apparatus are stored in the projection data storage unit 127. The projection data PD and the biological signal data TD are stored with its constituent data elements in a chronological order.

The projection data PD is also referred to as a raw data and it is a collection of data as a result of detection obtained by a continuous single scanning. Data immediately after the detection is referred to as pure raw data, and this pure raw data that has been corrected is referred to as the projection data. The continuous single scanning means the process of continuous emitting X-rays from the scan starting position till the scan completing position and of detecting the transmitted X-ray.

The biological signal data is the data, such as biological signal waveform, that TD shows the time change in the biological signal wave, or the electrocardiographic data that shows the heart rate or the respiration data showing the motion of the lung.

Figure 16:
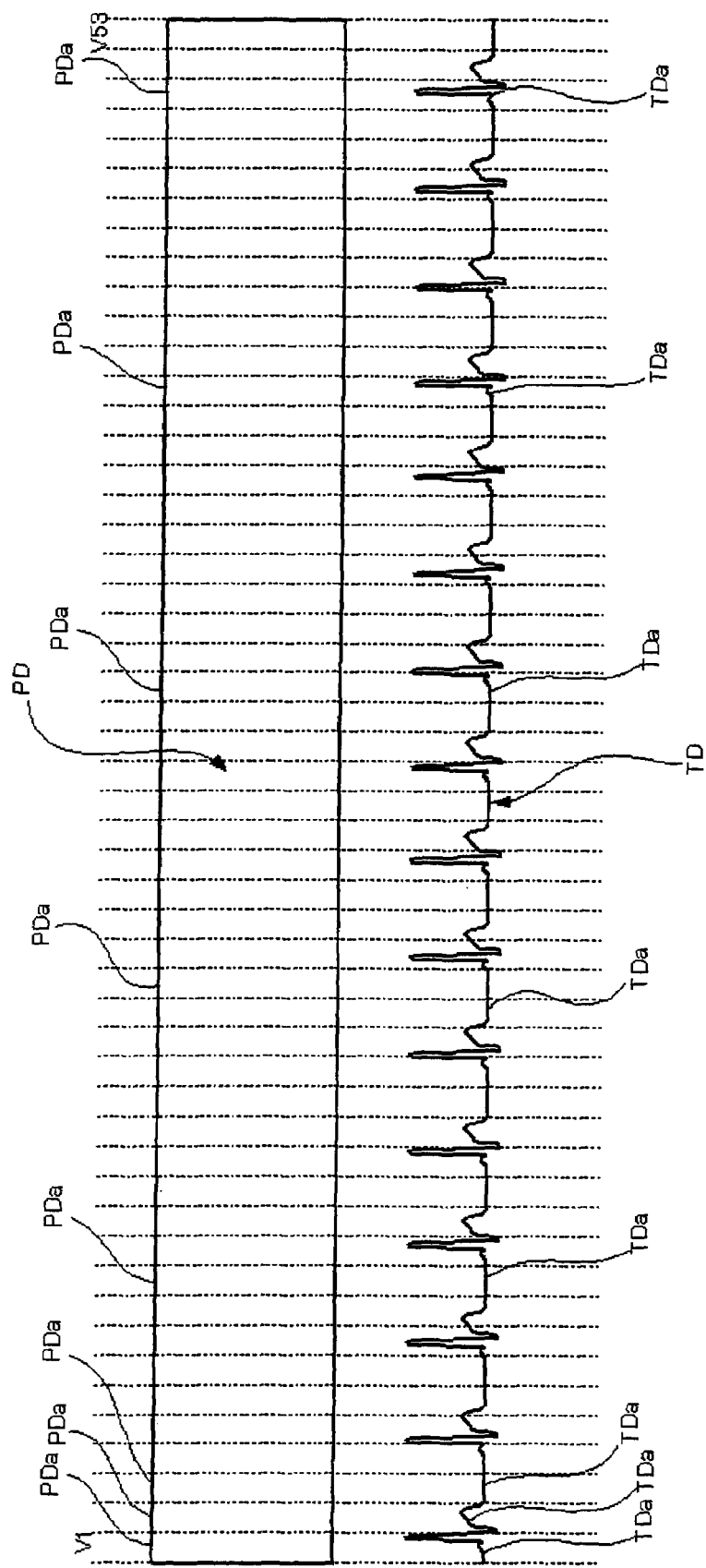
FIG. 16 is a diagram that shows projection data stored in the projection data storage unit as well as the biological signal data.

FIG. 16 is the diagram that shows the projection data PD stored in the projection data storage unit 127 and the biological signal data TD. A view number Vx (X: 1,2,3 . . . ) is numbered to the projection data PD, per partial data PDa that is an element of the projection data PD. The view number Vx is supplied in chronological order. A pair of partial data PDa that is per view of the projection data PD and partial data TDa of the biological signal data TD that is obtained at the same time as for partial data PDa is stored in the projection data storage unit 127.

The area segmenting unit 11 includes a central processing unit 1a and a main storage unit 1b in its structure. This area segmenting unit 11 segments the projection data PD into the partial data PDa (first projection data) of the reconstruction area SE reconstructed in synchronization with the biological signal and the partial data PDa of the reconstruction area NSE reconstructed in asynchronization with the biological signal (second projection data). This segmentation stores data that identifies the area of the partial data PDa against reconstruction area SE reconstructed in synchronization with the biological signal, and data that identifies the area of the partial data PDa against the reconstruction area NSE reconstructed in asynchronization with the biological signal. Such data is composed of the view number Vx. The area segmenting unit 11 stores the view number Vx of specified reconstruction area SE as the data that shows the reconstruction area SE reconstructed in synchronization with the biological signal, and the view number Vx of specified reconstruction area NSE as the data that shows the reconstruction area NSE reconstructed in asynchronization with the biological signal.

The area segmenting unit 11 stores the view number Vx of the reconstruction area SE and the view number Vx of the reconstruction area NSE, in a partly duplicated way. For example, the view numbers V1 to 30 are stored as the reconstruction area SE data and the view numbers V30 to 53 are as the reconstruction area NSE. In short, the view number V30 is stored as data showing the reconstruction area SE reconstructed in synchronization with the biological signal or as data showing the reconstruction area NSE reconstructed in asynchronization with the biological signal.

The biological signal synchronization reconstruction unit 128 includes the central processing unit lain its structure. This biological signal synchronization reconstruction unit 128 reconstructs the volume image from the projection data PD by the biological signal synchronization reconstruction method. The biological signal synchronization reconstruction method is the method that extracts the partial data PDa only that refracts a particular phase of the body motion, and reconstructs the volume image from the extracted partial data PDa. The example includes electrocardiographic synchronization reconstruction method, etc. This can convert particular phase of the body motion into an image with a high accuracy, so it is preferable to image the organ with the motion.

It is noted that, the projection data PD includes data for the zone in which the helical pitch is being changed via a variable helical scan, and also the volume image is generated from the data for this zone.

FIG. 17 is a pattern diagram of the biological signal synchronization reconstruction method. As shown in FIG. 17, the biological signal synchronization reconstruction unit 128 reads data of the reconstruction area SE reconstructed in synchronization with the biological signal from the area segmenting unit 11 (a in this figure), and extracts the partial data PDa supplied with each view number Vx showing the reconstruction area SE from the projection data PD stored in the projection data storage unit 127 (b to c in this figure). At the same time, from the biological signal data TD, the partial data TDa that is stored as a pair with the read partial data PDa is extracted (b to c in this figure).

From the partial data TDa of the read biological signal data TD, the partial data TDa obtained at the time of a particular phase is searched (c to d in this figure), and the partial data PDa of the projection data PD that is paired with the searched partial data TDa is further extracted and collected (d to e in this figure). For example, when the biological signal data TD is the electrocardiographic data, partial data TDa that shows the noncontractile timing between the heart rate cycles is searched, and also the partial data PDa of the projection data PD that is paired with the partial data TDa is extracted.

It is noted that, instead of directly searching partial data TDa that shows the non-contractile timing between heartbeat cycles, the partial data PDa that corresponds to the R wave may searched and, partial data PDa of the projection data PD obtained after a predetermined period of time from the partial data PDa may be extracted as the non-contractile timing.

The biological signal synchronization reconstruction unit 128 performs the reconstruction process using the 3D image reconstruction algorithm that is represented from the finally extracted multiple partial data PDa to the Feldkamp method, to reconstruct the volume image that is created by collecting the multiple voxel data in 3D (e to f in this figure).

The biological signal asynchronization reconstruction unit 129 includes the central processing unit 1a in its structure. The biological signal asynchronization reconstruction unit 129, regardless of the biological signal synchronization reconstruction method, performs reconstruction process by 3D image reconstruction algorithm that is typically Feldkamp method, without being synchronized with the biological signal data.

FIG. 18 is a pattern diagram that reconstructs in asynchronization with the biological signal. As shown in FIG. 18, the biological signal asynchronization reconstruction unit 129 reads, from the area segmenting unit 11, data for reconstruction area NSE that is reconstructed in asynchronization with the biological signal (a in this figure), and then reads the partial data PDa of the projection data PD that is numbered with the view number Vx showing the reconstruction area NSE from the projection data storage unit 127 (b to c in this figure). Thus read entire partial data PDa is now processed for reconstruction by the algorithm like 3D image reconstruction that is typically Feldkamp method, to reconstruct the volume image in which multiple voxel data is gathered in 3D (c to d in this figure).

The combining unit 14 includes the central processing unit 1a in its structure. The combining unit 14 combines the volume image reconstructed by the biological signal synchronization reconstruction unit 128 and the volume image reconstructed by the biological signal asynchronization reconstruction unit 129 so as to order them in the order of the view number Vx. Overlapped volume images are combined by the feathering process. The volume images combined by the combining unit 14 are displayed as a single image on the monitor 124.

Figure 19:
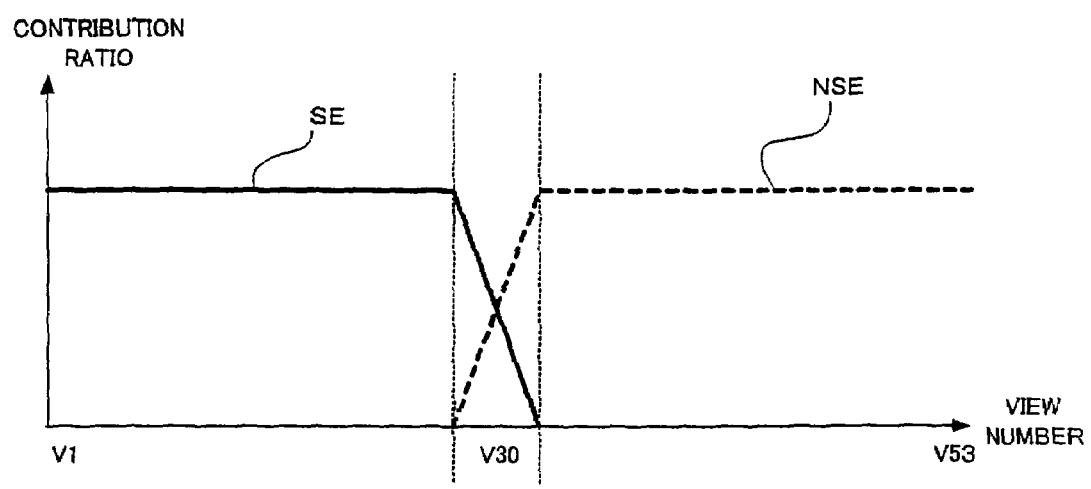
FIG. 19 is a diagram that shows the feathering process.

FIG. 19 is the diagram that shows the feathering process. The feathering means a process to add a gradation of contribution ratio to the overlapping area of both volume images. The contribution ratio is the ratio of occupation in displaying that area, and less contribution ratio means more transparency. As for the area of both overlapped volume images, the contribution ratio is reduced as closer to the edge of the image. The volume images that are reconstructed separately will look more natural by the feathering process, enabling to see it as an integrated image visually.

In short, the combining unit 14 reads the weighting function reconstructing the contribution ratio shown in FIG. 19 from the external storage unit 1c, and using this weighting function, while weighting each volume data that constructs the volume image, adds both volume images per view number. This weighting function is the function that remains the same until the vicinity of the volume image boundary, and whose contribution ratio is decreased as approaching from the vicinity of the volume image boundary to the boundary.

Figure 20:
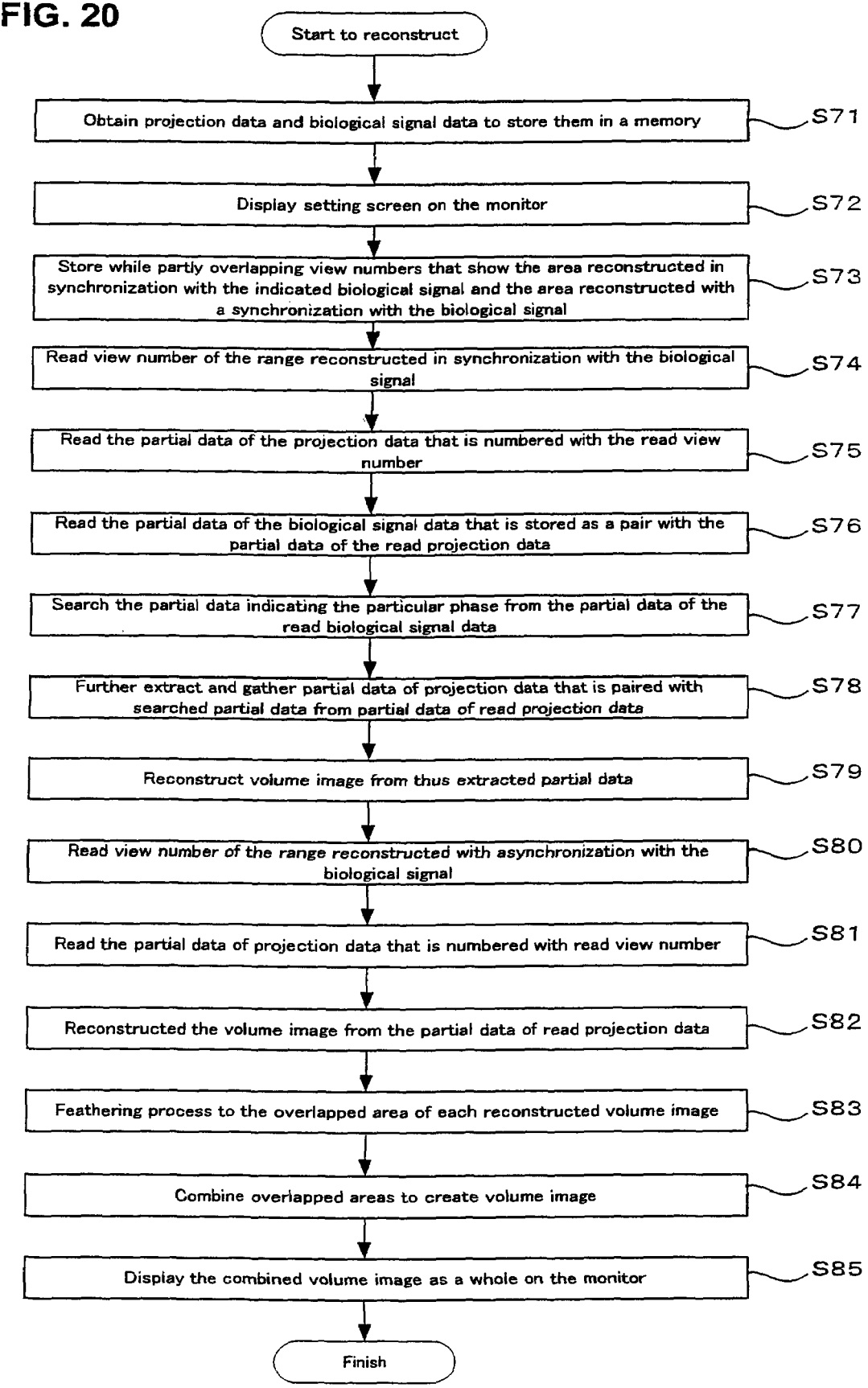
FIG. 20 is a flowchart that shows the operation of the image reconstruction process.

The image reconstruction process operation of this image reconstruction processing apparatus is explained with reference to FIG. 20. FIG. 20 is a flow chart that shows the operation of the image reconstruction process operation.

First, the image reconstruction processing apparatus obtains the projection data PD and biological signal data TD and stores them in the storage area (S71). If the image reconstruction processing apparatus is included in X-ray CT apparatus that is described later, the projection data PD obtained by scanning the subject to be examined and the biological signal data TD obtained during the scan are stored. If the image reconstruction processing apparatus is consisted of other computer than X-ray CT apparatus, it is obtained via a network or a portable memory device.

Next, image reconstruction processing apparatus, after the command is input by the image reconstruction process using the input unit 123, displays the setting screen on the monitor 124 (S72). The setting screen displays the pattern diagram of the subject to be examined SG. For this setting screen, by way of the input unit 123 by the operator, the reconstruction area SE reconstructed in synchronization with the biological signal with reference to the pattern diagram SG of the subject to be examined and the reconstruction area NSE reconstructed in asynchronization with the biological signal are indicated.

When the reconstruction area SE reconstructed in synchronization with the biological signal and the reconstruction area NSE reconstructed in asynchronization with the biological signal are indicated, the image reconstruction processing apparatus stores the view number Vx that shows the reconstruction area SE in synchronization with the indicated biological signal and the view number Vx that shows the reconstruction area NSE reconstructed in asynchronization with the biological signal in a partly overlapped way in the memory (S73).

It is noted that, if the image reconstruction processing apparatus is included in X-ray CT apparatus, data indicating the reconstruction area NSE reconstructed in asynchronization with the biological signal and the reconstruction area SE reconstructed in synchronization with the indicated biological signal is stored in advance, at the steps of S72 to S73, and then the projection data PD and biological signal data TD at the S01 is stored sequentially during the scan.

When projection data PD and biological signal data TD, as well as the data for the reconstruction area SE reconstructed in synchronization with the biological signal and the reconstruction area NSE in asynchronization with the biological signal are stored, image reconstruction processing apparatus performs the reconstruction process of the volume image.

Firstly, image reconstruction processing apparatus reads a view number Vx of the reconstruction area SE that is reconstructed in synchronization with the biological signal (S74). When the view number Vx of the reconstruction area SE is read, the partial data PDa of the projection data PD to which this view number Vx is attached is read (S75). At the same time, the partial data TDa of biological signal data TD that is stored as a pair with the partial data PDa is read (S76).

When the partial data TDa of the biological signal data TD is read, the image reconstruction processing apparatus searches the partial data TDa that shows a particular phase among this partial data TDa (S77). This search, in order to search the phase of the physical movement at the noncontractile period for example, if the biological signal data TD is the electrocardiographic data, it searches the partial data TDa which a specified number of seconds have passed from Q wave. When partial data TDa showing the particular phase is searched, the partial data PDa of the projection data PD that is paired with this partial data TDa is further extracted from the read partial data PDa and gathered (S78).

When the partial data PDa that shows the particular phase of the reconstruction area SE reconstructed in synchronization with the biological signal is extracted from the projection data PD, the image reconstruction processing apparatus reconstructs the volume image from this extracted partial data PDa (S79). The reconstructed volume image is kept temporally.

Furthermore, the image reconstruction processing apparatus reads view number Vx of the reconstruction area NSE that is reconstructed in asynchronization with the biological signal (S80). When the view number Vx of the reconstruction area NSE is read, partial data PDa of the projection data PD in which this view number Vx is supplied (S81). When the partial data PDa that corresponds to the reconstruction area NSE is read, the image reconstruction processing apparatus reconstructs, from this partial data PDa, the volume image (S82). The reconstructed volume image is temporarily kept.

It is noted that the processing order may be changeable, as for reconstruction of the volume image of the reconstruction area SE reconstructed in synchronization of the biological signal of S75 to S79, and as for that of the volume image of the reconstruction area NSE reconstructed in asynchronization with the biological signal of S80 to S82.

Assume that the reconstruction area SE is reconstructed into the volume image by the biological signal synchronization reconstruction method, while the reconstruction area NSE is reconstructed, regardless of synchronization of the biological signal, into the volume image. In this case, the image reconstruction processing apparatus performs the feathering process to each overlapping area of volume images (S83), and superimposes such overlapped area to combine the volume image (S84). When the volume images are combined, the image reconstruction processing apparatus displays the combined volume image entirely on the monitor 124 (S85).

It is noted that, this feathering process can be performed prior to obtaining the projection data PD, which means it can be performed to pure raw data in advance.

In this way, according to the image reconstruction processing technology of this embodiment, the projection data PD obtained during a single scan is segmented into the reconstruction area SE reconstructed in synchronization with the biological signal and the reconstruction area NSE reconstructed in asynchronization with the biological signal, and then a volume image is formed by a separate method for reconstructing the image. As a result, even if the reconstruction area SE reconstructed in synchronization with the biological signal is scanned while reducing the moving speed of the bed board 112b or the reconstruction area SE reconstructed in synchronization with the biological signal and the reconstruction area NSE reconstructed in asynchronization with the biological signal are scanned at the same time, it will not cause the time lag between the reconstruction area SE reconstructed in synchronization with the biological signal and the reconstruction area NSE reconstructed in asynchronization with the biological signal, and also the volume image that does not cause inaccuracy in the area involving movement can be reconstructed.

Also, thanks to the feathering process, volume images reconstructed separately look more natural, so it is visually possible to be grasped as an integrated image.

It is noted that, change of the moving speed of the bed board 112b may be accompanied with the change of the number of lines of X-ray detecting elements provided by the detector 111c. Also, even when the bed board 112b is being accelerated, emission of X-rays is continued, and the image is reconstructed from the projection data PD of the emission area. The scan-controlling unit 122 outputs the driving signal of current value that corresponds to the moving speed set for the reconstruction area NSE onto the bed-driving unit 112c. Also, segmentation of the reconstruction area SE reconstructed in synchronization with the biological signal and reconstruction area NSE reconstructed in asynchronization with the biological signal may be performed to the transmission data only, and it can be segmented at the time of projection data or pure raw data.

What is claimed is:

1. An X-ray computed tomography (CT) apparatus having an X-ray tube emitting an X-ray, a detector detecting X-rays transmitted through a subject to be examined, and a bed on which said subject to be examined is placed, said X-ray CT apparatus reconstructing an image of the subject to be examined from a transmission data obtained by detecting the emitted X-rays transmitted through the subject to be examined, comprising:
   an input part configured to specify an area of the subject which is to be reconstructed in synchronization with a biological signal of the subject and an area which is to be reconstructed in asynchronization with the biological signal;
   a scan controlling part configured to perform a continuous single helical scan by moving said X-ray tube and said detector relative to said bed, and also to change a moving speed of said bed during the continuous single helical scan;
   a detecting part configured to detect the biological signal of the subject to be examined;
   a memory part configured to store the transmission data obtained during said helical scan and the said biological signal data in a correlated way;
   a segmentation part configured to segment said transmission data into a first transmission data that corresponds to the area to be reconstructed in synchronization with said biological signal and a second transmission data that corresponds to the area to be reconstructed in asynchronization with said biological signal, while a region corresponding to an area on both sides of a boundary between the synchronization area to be reconstructed and the asynchronization area to be reconstructed belongs to both the first transmission data and the second transmission data;
   a biological-signal synchronization reconstructing part configured to reconstruct a synchronized image of said subject to be examined based on said biological signal data and said first transmission data including data from the region corresponding to the area on both sides of the boundary;
   a biological-signal asynchronization reconstructing part configured to reconstruct an asynchronized image of said subject to be examined from said second transmission data including data from the region corresponding to the area on both sides of the boundary without using said biological signal data; and
   a combining part configured to create a combined image from said synchronized image and said asynchronized image such that the synchronized image reconstructed by said biological-signal synchronization reconstructing part and the asynchronized image reconstructed by said biological-signal asynchronization reconstructing part are combined with weighting addition at said region corresponding to the area on both sides of the boundary.

2. The X-ray CT apparatus according to claim 1, wherein said scan controlling part slows down the moving speed of said bed to a speed such that the biological signal for multiple cycles can be detected, during the helical scan of the area to be reconstructed in synchronization with said biological signal.

3. The X-ray CT apparatus according to claim 1, wherein said combining part gradually changes said weighting in the vicinity of an end of said synchronized image and said asynchronized image.

4. The X-ray CT apparatus according to claim 1, wherein said detecting part is an electrocardiographic equipment that detects heart rate of the subject to be examined and creates electrocardiographic data, and said memory part stores such data as said biological signal data.

5. The X-ray CT apparatus according to claim 1, wherein said detecting part is a respiration sensor that detects respiration of the subject to be examined and creates respiration data, and said memory part stores such data as said biological signal data.

6. An image reconstruction processing apparatus, comprising:
   an input part configured to specify an area which is to be reconstructed in synchronization with a biological signal and an area which is to be reconstructed in asynchronization with the biological signal;
   a memory part configured to store transmission data obtained by a continuous single helical scan and biological signal data of the subject to be examined obtained during said helical scan in a correlated way;
   a segmentation part configured to segment said transmission data into a first transmission data that corresponds to the area to be reconstructed in synchronization with said biological signal and a second transmission data that corresponds to the area to be reconstructed in asynchronization with said biological signal, while a region corresponding to an area on both sides of a boundary between the synchronization area to be reconstructed and the asynchronization area to be reconstructed belongs to both the first transmission data and the second transmission data;
   a biological-signal synchronization reconstructing part configured to reconstruct a synchronized image of said subject to be examined based on said biological signal data and said first transmission data including data from the region corresponding to the area on both sides of the boundary;
   a biological-signal asynchronization reconstructing part configured to reconstruct an asynchronized image of said subject to be examined from said second transmission data including data from the region corresponding to the area on both sides of the boundary without using said biological signal data; and
   a combining part configured to create a combined image from said synchronized image and said asynchronized image such that the synchronized image reconstructed by said biological-signal synchronization reconstructing part and the asynchronized image reconstructed by said biological-signal asynchronization reconstructing part are combined with weighting addition at said region corresponding to the area on both sides of the boundary.

7. An X-ray computed tomography (CT) image reconstruction processing apparatus according to claim 6, wherein said combining part gradually changes said weighting in the vicinity of an end of said synchronized image and said asynchronized image.

8. The image reconstruction processing apparatus according to claim 6, wherein said memory part stores electrocardiographic data as said biological signal data.

9. The image reconstruction processing apparatus according to claim 6, wherein said memory part stores respiration data as said biological signal data.

10. An image reconstruction processing method comprising:
   storing transmission data of a subject to be examined obtained by a continuous single helical scan and a biological signal data of the subject to be examined obtained during said helical scan;

segmenting said transmission data into a first transmission data that corresponds to an area to be reconstructed in synchronization with said biological signal and a second transmission data that corresponds to an area to be reconstructed in asynchronization with said biological signal, while a region corresponding to an area on both sides of a boundary between the synchronization area to be reconstructed and the asynchronization area to be reconstructed belongs to both the first transmission data and the second transmission data;

reconstructing a synchronized image of said subject to be examined based on said biological signal data and said first transmission data including data from the region corresponding to the area on both sides of the boundary;

reconstructing an asynchronized image of said subject to be examined from said second transmission data including data from the region corresponding to the area on both sides of the boundary without using said biological signal data; and creating a combined image from said synchronized image and said asynchronized image such that the synchronized image reconstructed in said reconstruction with synchronization and the asynchronized image reconstructed in said reconstruction with asynchronization are combined with weighting addition at said region corresponding to the area on both sides of the boundary.

11. The image reconstruction processing method according to claim 10, wherein said weighting gradually changes in the vicinity of an end of said synchronized image and said asynchronized image in said creation of the combined image.

12. The image reconstruction processing method according to claim 11, wherein electrocardiographic data is stored as said biological signal data.

13. The image reconstruction processing method according to claim 12, wherein respiration data is stored as said biological signal data.

14. A computer readable medium storing program instructions which when executed by a computer results in performance of steps for image reconstruction processing, comprising:

specifying an area which is to be reconstructed in synchronization with a biological signal of a subject to be examined and an area which is to be reconstructed in asynchronization with the biological signal on the computer;

storing transmission data obtained during a continuous single helical scan and biological signal data of the subject to be examined obtained during said continuous single helical scan in a correlated way;

segmenting said transmission data into a first transmission data that corresponds to the area to be reconstructed in synchronization with said biological signal and a second transmission data that corresponds to the area to be reconstructed in asynchronization with said biological signal, while a region corresponding to an area on both sides of a boundary between the synchronization area to be reconstructed and the asynchronization area to be reconstructed belongs to both the first transmission data and the second transmission data;

reconstructing a synchronized image of said subject to be examined based on said biological signal data and said first transmission data including data from the region corresponding to the area on both sides of the boundary;

reconstructing an asynchronized image of said subject to be examined from said second transmission data including data from the region corresponding to the area on both sides of the boundary without using said biological signal data; and creating a combined image from said synchronized image and said asynchronized image such that the synchronized image reconstructed in said reconstruction with synchronization and the asynchronized image reconstructed in said reconstruction with asynchronization are combined with weighting addition at said region corresponding to the area on both sides of the boundary.

15. A computer readable medium according to claim 14, wherein said weighting gradually changes in the vicinity of an end of said synchronized image and said asynchronized image.

16. A computer readable medium according to claim 14, wherein electrocardiographic data is stored as said biological signal data.

17. A computer readable medium according to claim 14, wherein respiration data is stored as said biological signal data.

* * * * *